(12) United States Patent
Foo et al.

(10) Patent No.: US 7,709,674 B2
(45) Date of Patent: May 4, 2010

(54) HYDROCYANATION PROCESS WITH REDUCED YIELD LOSSES

(75) Inventors: Thomas Foo, Wilmington, DE (US); James Michael Garner, Wilmington, DE (US); Ron Ozer, Wilmington, DE (US); Paul S. Pearlman, Thornton, PA (US)

(73) Assignee: Invista North America S.A R.L, Wilmington, DE (US)

( * ) Notice: Subject to any disclaimer, the term of this patent is extended or adjusted under 35 U.S.C. 154(b) by 81 days.

(21) Appl. No.: 11/776,968

(22) Filed: Jul. 12, 2007

(65) Prior Publication Data

US 2008/0015382 A1    Jan. 17, 2008

Related U.S. Application Data

(60) Provisional application No. 60/830,986, filed on Jul. 14, 2006.

(51) Int. Cl.
C07C 253/00    (2006.01)
(52) U.S. Cl. .................................. 558/332; 558/338
(58) Field of Classification Search ............... 558/332, 558/338
See application file for complete search history.

(56) References Cited

U.S. PATENT DOCUMENTS

| | | | |
|---|---|---|---|
| 2,402,873 A | 6/1946 | Coffman et al. |
| 2,570,199 A | 10/1951 | Brown |
| 2,583,984 A | 1/1952 | Arthur, Jr. |
| 2,666,780 A | 1/1954 | Arthur, Jr. |
| 3,282,981 A | 11/1966 | Davis |
| 3,297,742 A | 1/1967 | Clarke, Jr. |
| 3,328,443 A | 6/1967 | Clark |
| 3,340,207 A | 9/1967 | Baker |
| 3,496,210 A | 2/1970 | Drinkard, Jr. |
| 3,496,215 A | 2/1970 | Drinkard et al. |
| 3,496,217 A | 2/1970 | Drinkard et al. |
| 3,496,218 A | 2/1970 | Drinkard et al. |
| 3,522,288 A | 7/1970 | Drinkard, Jr. |
| 3,526,654 A | 9/1970 | Hildebrand |
| 3,536,748 A | 10/1970 | Drinkard et al. |
| 3,538,142 A | 11/1970 | Drinkard, Jr. |
| 3,542,847 A | 11/1970 | Drinkard, Jr. |
| 3,547,972 A | 12/1970 | Drinkard, Jr. |
| 3,551,474 A | 12/1970 | Drinkard, Jr. |
| 3,563,698 A | 2/1971 | Rushmere |
| 3,564,040 A | 2/1971 | Downing et al. |
| 3,579,560 A | 5/1971 | Drinkard, Jr. |
| 3,631,191 A | 12/1971 | Kane et al. |
| 3,641,107 A | 2/1972 | Breda |
| 3,651,146 A | 3/1972 | Schritlz |
| 3,652,641 A | 3/1972 | Druliner |
| 3,655,723 A | 4/1972 | Drinkard |
| 3,676,475 A | 7/1972 | Drinkard, Jr. |
| 3,676,481 A | 7/1972 | Chia |
| 3,694,485 A | 9/1972 | Drinkard, Jr. |
| 3,739,011 A | 6/1973 | Drinkard |
| 3,752,839 A | 8/1973 | Drinkard |
| 3,766,231 A | 10/1973 | Wayne |
| 3,766,237 A | 10/1973 | Chia et al. |
| 3,766,241 A | 10/1973 | Drinkard |
| 3,773,809 A | 11/1973 | Walter |
| 3,775,461 A | 11/1973 | Drinkard |
| 3,798,256 A | 3/1974 | King |
| 3,818,067 A | 6/1974 | Downing |
| 3,818,068 A | 6/1974 | Wells |
| 3,846,461 A | 11/1974 | Shook |
| 3,846,474 A | 11/1974 | Mok |
| 3,847,959 A | 11/1974 | Shook |
| 3,850,973 A | 11/1974 | Seidel |
| 3,852,325 A | 12/1974 | King |
| 3,852,327 A | 12/1974 | King |
| 3,852,328 A | 12/1974 | Chia |
| 3,852,329 A | 12/1974 | Tomlinson |
| 3,853,754 A | 12/1974 | Gosser |
| 3,853,948 A | 12/1974 | Drinkard |

(Continued)

FOREIGN PATENT DOCUMENTS

DE    100 460 25    3/2002

(Continued)

OTHER PUBLICATIONS

C. A. Tolman et al.—"Homogeneous Nickel-Catalyzed Olefin Hydrocyanation", Advances in Catalysis, vol. 33, p. 1 (1985).
C. A. Tolman et al.—"Homogeneous Nickel-Catalyzed Olefin Hydrocyanation", Advances in Catalysis, vol. 33, pp. 23-24, 31-34, 37-38 and 41 (1985).

*Primary Examiner*—Kamal A Saeed
*Assistant Examiner*—Samantha L Shterengarts
(74) *Attorney, Agent, or Firm*—Robert B. Furr, Jr.; Thomas W. Steinberg

(57) ABSTRACT

A hydrocyanation process produces adiponitrile and other dinitriles having six carbon atoms. The process involves forming a reaction mixture in the presence of at least one Lewis acid. The reaction mixture includes ethylenically unsaturated nitriles having five carbon atoms, hydrogen cyanide, and a catalyst precursor compositions. The reaction mixture is continuously fed while controlling the overall feed molar ratio of 2-pentenenitriles to all unsaturated nitriles and the overall feed molar ratio of hydrogen cyanide to all unsaturated nitriles. In the reaction product mixture, including adiponitrile, the ratio of the concentration of 2-pentenenitriles to the concentration of 3-pentenenitriles from about 0.2/1 to about 10/1. Included in the catalyst precursor composition is a zero-valent nickel and at least one multidentate phosphorus-containing ligand. The multidentate phosphorus-containing ligand may be a phosphite, a phosphonite, a phosphinite, a phosphine, and a mixed phosphorus-containing ligand or a combination of such members.

19 Claims, No Drawings

U.S. PATENT DOCUMENTS

| | | | |
|---|---|---|---|
| 3,859,327 | A | 1/1975 | Wells |
| 3,864,380 | A | 2/1975 | King |
| 3,865,865 | A | 2/1975 | Musser et al. |
| 3,884,997 | A | 5/1975 | Shook, Jr. |
| 3,903,120 | A | 9/1975 | McGill |
| 3,920,721 | A | 11/1975 | Gosser |
| 3,925,445 | A | 12/1975 | King |
| 3,927,056 | A | 12/1975 | Gosser |
| 3,983,011 | A | 9/1976 | Wiggill |
| 3,997,579 | A | 12/1976 | Jesson |
| 4,045,495 | A | 8/1977 | Nazarenko |
| 4,046,815 | A | 9/1977 | Nazarenko |
| 4,076,756 | A | 2/1978 | Nazarenko |
| 4,080,374 | A | 3/1978 | Corn |
| 4,082,811 | A | 4/1978 | Shook, Jr. |
| 4,134,923 | A | 1/1979 | Reimer |
| 4,146,555 | A | 3/1979 | Kershaw |
| 4,147,717 | A | 4/1979 | Kershaw |
| 4,177,215 | A | 12/1979 | Seidel |
| 4,251,468 | A | 2/1981 | Nazarenko |
| 4,298,546 | A | 11/1981 | McGill |
| 4,328,172 | A | 5/1982 | Rapoport |
| 4,330,483 | A | 5/1982 | Rapoport |
| 4,336,110 | A | 6/1982 | Reimer |
| 4,339,395 | A | 7/1982 | Barnette |
| 4,347,193 | A | 8/1982 | Shook, Jr. |
| 4,371,474 | A | 2/1983 | Rapoport |
| 4,382,038 | A | 5/1983 | McGill |
| 4,385,007 | A | 5/1983 | Shook, Jr. |
| 4,387,056 | A | 6/1983 | Stowe |
| 4,394,321 | A | 7/1983 | Cone |
| 4,416,824 | A | 11/1983 | Reimer |
| 4,416,825 | A | 11/1983 | Ostermaier |
| 4,434,316 | A | 2/1984 | Barnette |
| 4,510,327 | A | 4/1985 | Peet |
| 4,521,628 | A | 6/1985 | Ostermaier |
| 4,539,302 | A | 9/1985 | Leyendecker |
| 4,705,881 | A | 11/1987 | Rapoport |
| 4,714,773 | A | 12/1987 | Rapoport |
| 4,750,881 | A | 3/1988 | Kikuchi et al. |
| 4,749,801 | A | 6/1988 | Beatty |
| 4,774,353 | A | 9/1988 | Hall et al. |
| 4,783,546 | A | 11/1988 | Burke |
| 4,810,815 | A | 3/1989 | Bryndza |
| 4,874,884 | A | 10/1989 | McKinney et al. |
| 4,990,645 | A | 2/1991 | Back |
| 5,087,723 | A | 2/1992 | McKinney |
| 5,107,012 | A | 4/1992 | Grunewald |
| 5,143,873 | A | 9/1992 | Bryndza |
| 5,175,335 | A | 12/1992 | Casalnuovo |
| 5,312,957 | A | 5/1994 | Casalnuovo |
| 5,312,959 | A | 5/1994 | Sieja |
| 5,382,697 | A | 1/1995 | Casalnuovo |
| 5,440,067 | A | 8/1995 | Druliner |
| 5,449,807 | A | 9/1995 | Druliner |
| 5,484,902 | A | 1/1996 | Casalnuovo |
| 5,510,470 | A | 4/1996 | Casalnuovo |
| 5,512,695 | A | 4/1996 | Kreutzer et al. |
| 5,512,696 | A | 4/1996 | Kreutzer et al. |
| 5,523,453 | A | 6/1996 | Breikss |
| 5,543,536 | A | 8/1996 | Tam |
| 5,663,369 | A | 9/1997 | Kreutzer |
| 5,688,986 | A | 11/1997 | Tam et al. |
| 5,693,843 | A | 12/1997 | Breikss et al. |
| 5,696,280 | A | 12/1997 | Shapiro |
| 5,709,841 | A | 1/1998 | Reimer |
| 5,723,641 | A | 3/1998 | Tam et al. |
| 5,821,378 | A | 10/1998 | Foo et al. |
| 5,847,191 | A | 12/1998 | Bunel et al. |
| 5,959,135 | A | 9/1999 | Garner et al. |
| 5,981,772 | A | 11/1999 | Foo et al. |
| 6,020,516 | A | 2/2000 | Foo et al. |
| 6,031,120 | A | 2/2000 | Tam |
| 6,048,996 | A | 4/2000 | Clarkson |
| 6,069,267 | A | 5/2000 | Tam |
| 6,077,979 | A | 6/2000 | Qiu |
| 6,120,700 | A | 9/2000 | Foo et al. |
| 6,121,184 | A | 9/2000 | Druliner |
| 6,127,567 | A | 10/2000 | Garner et al. |
| 6,171,996 | B1 | 1/2001 | Garner et al. |
| 6,171,997 | B1 | 1/2001 | Foo |
| 6,242,633 | B1 | 6/2001 | Fischer et al. |
| 6,284,865 | B1 | 9/2001 | Tam et al. |
| 6,362,354 | B1 | 3/2002 | Bunel |
| 6,372,147 | B1 | 4/2002 | Reimer |
| 6,380,421 | B1 | 4/2002 | Lu |
| 6,399,534 | B2 | 6/2002 | Bunel |
| 6,420,611 | B1 | 7/2002 | Tam |
| 6,461,481 | B1 | 10/2002 | Barnette |
| 6,489,517 | B1 | 12/2002 | Shapiro |
| 6,521,778 | B1 | 2/2003 | Fischer et al. |
| 6,555,718 | B1 | 4/2003 | Shapiro |
| 6,646,148 | B1 | 11/2003 | Kreutzer et al. |
| 6,660,876 | B2 | 12/2003 | Gagne |
| 6,660,877 | B2 | 12/2003 | Lenges et al. |
| 6,737,539 | B2 | 5/2004 | Lenges |
| 6,753,440 | B2 | 6/2004 | Druliner |
| 6,770,770 | B1 | 8/2004 | Baumann et al. |
| 6,812,352 | B2 | 11/2004 | Kreutzer |
| 6,844,289 | B2 | 1/2005 | Jackson |
| 6,846,945 | B2 | 1/2005 | Lenges |
| 6,855,799 | B2 | 2/2005 | Tam |
| 6,893,996 | B2 | 5/2005 | Chu et al. |
| 6,897,329 | B2 | 5/2005 | Jackson |
| 6,906,218 | B2 | 6/2005 | Allgeier |
| 6,924,345 | B2 | 8/2005 | Gagne et al. |
| 6,936,171 | B2 | 8/2005 | Jackson et al. |
| 6,984,604 | B2 | 1/2006 | Cobb |
| 7,022,866 | B2 | 4/2006 | Bartsch et al. |
| 7,071,365 | B2 | 7/2006 | Lu |
| 7,528,275 | B2 * | 5/2009 | Bartsch et al. ............... 558/332 |
| 2003/0100802 | A1 | 5/2003 | Shapiro |
| 2003/0100803 | A1 | 5/2003 | Lu et al. |
| 2003/0135014 | A1 | 7/2003 | Radu et al. |
| 2004/0106815 | A1 | 6/2004 | Ritter |
| 2004/0176622 | A1 | 9/2004 | Bartsch et al. |
| 2005/0059737 | A1 | 3/2005 | Allgeier |
| 2005/0090677 | A1 | 4/2005 | Bartsch et al. |
| 2005/0090678 | A1 | 4/2005 | Bartsch et al. |
| 2005/0159614 | A1 | 7/2005 | Allgeier |
| 2007/0219386 | A1 | 9/2007 | Ritter |
| 2008/0015378 | A1 | 1/2008 | Foo |
| 2008/0015379 | A1 | 1/2008 | Garner |
| 2008/0015380 | A1 | 1/2008 | Foo |
| 2008/0015381 | A1 | 1/2008 | Foo |
| 2008/0015382 | A1 | 1/2008 | Foo |

FOREIGN PATENT DOCUMENTS

| | | |
|---|---|---|
| EP | 1528054 A1 | 5/2005 |
| WO | WO99/06358 | 2/1999 |
| WO | WO01/14392 | 3/2001 |
| WO | WO02/13964 | 2/2002 |
| WO | WO2005/042547 | 5/2005 |
| WO | WO2005/073172 A1 | 8/2005 |

* cited by examiner

HYDROCYANATION PROCESS WITH REDUCED YIELD LOSSES

CROSS-REFERENCE TO RELATED APPLICATIONS

This application claims benefit of priority from Provisional Application No. 60/830,986, filed Jul. 14, 2006. This application hereby incorporates by reference Provisional Application No. 60/830,986 in its entirety. This application relates to commonly-assigned applications filed concurrently on Jul. 12, 2007.

FIELD OF THE INVENTION

The present process is directed to the hydrocyanation of ethylenically unsaturated nitriles having five carbon atoms to produce adiponitrile (ADN) and other dinitriles. More particularly, this invention relates to a process for the hydrocyanation of 3-pentenenitriles (3PN) and/or 4-pentenenitrile (4PN), and optionally 2-pentenenitriles (2PN), using a catalyst precursor composition comprising a zero-valent nickel and at least one multidentate phosphorus-containing ligand in the presence of at least one Lewis acid promoter.

BACKGROUND OF THE INVENTION

Hydrocyanation catalyst systems, particularly pertaining to the hydrocyanation of ethylenically unsaturated compounds, have been described. For example, systems useful for the hydrocyanation of 1,3-butadiene (BD) to form pentenenitrile (PN) isomers and in the subsequent hydrocyanation of pentenenitriles to form adiponitrile (ADN) are known in the commercially important nylon synthesis field.

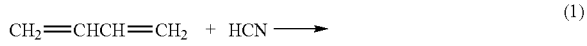

(1)

$CH_2 = CHCH = CH_2 + HCN \longrightarrow$ 1,3-Butadiene

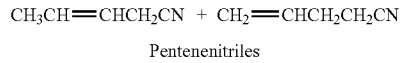

$CH_3CH = CHCH_2CN + CH_2 = CHCH_2CH_2CN$

Pentenenitriles

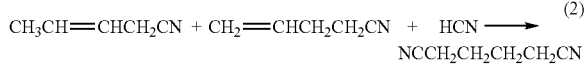

(2)

$CH_3CH = CHCH_2CN + CH_2 = CHCH_2CH_2CN + HCN \longrightarrow$
$NCCH_2CH_2CH_2CH_2CN$ The hydrocyanation of ethylenically unsaturated compounds using transition metal complexes with monodentate phosphite ligands is recited in the prior art. See, for example, U.S. Pat. Nos. 3,496,215; 3,631,191; 3,655,723; and 3,766,237, and Tolman et. al., *Advances in Catalysis*, 1985, 33, 1. Improvements in the zero-valent nickel catalyzed hydrocyanation of ethylenically unsaturated compounds with the use of certain multidentate phosphite ligands are also disclosed. Such improvements are described, for example, in U.S. Pat. Nos. 5,821,378; 5,981,772; 6,020,516; and 6,284,865.

The hydrocyanation of activated ethylenically unsaturated compounds, such as with conjugated ethylenically unsaturated compounds (e.g., BD and styrene), and strained ethylenically unsaturated compounds (e.g., norbornene) proceed at useful rates without the use of a Lewis acid promoter. However, hydrocyanation of unactivated, ethylenically unsaturated compounds, such as 1-octene and 3PN, requires the use of a Lewis acid promoter to obtain industrially useful rates and yields for the production of linear nitriles, such as n-octyl cyanide and ADN, respectively.

The use of a promoter in the hydrocyanation reaction is disclosed, for example, in U.S. Pat. No. 3,496,217. This patent discloses an improvement in hydrocyanation using a promoter selected from a large number of metal cation compounds as nickel catalyst promoters with a wide variety of counterions. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including pentenenitriles, in the presence of a zero-valent nickel catalyst and a triorganotin promoter. Moreover, U.S. Pat. No. 4,874,884 discloses a process for producing ADN by the zero-valent nickel catalyzed hydrocyanation of pentenenitriles in the presence of a synergistic combination of promoters selected in accordance with the desired reaction kinetics of the ADN synthesis. Furthermore, the use of Lewis acids to promote the hydrocyanation of pentenenitriles to produce ADN using zero-valent nickel catalysts with multidentate phosphite ligands is also disclosed. See, for example, U.S. Pat. Nos. 5,512,696; 5,723,641; 5,959,135; 6,127,567; and 6,646,148.

It is reported in the prior art that, concomitant with the hydrocyanation of 3PN and 4PN to produce ADN, some isomerization of 3PN to cis- and trans-2PN can occur. However, in the process of hydrocyanating 3PN and 4PN using nickel catalysts derived from monodentate phosphite ligands, such as $Ni[P(OC_6H_5)_3]_4$, U.S. Pat. No. 3,564,040 states that the presence of 2PN, even in low concentrations, is detrimental to catalyst efficiency and the production of 2PN is undesirable since they constitute a yield loss as well as a poison for the catalyst.

In order to address this issue, U.S. Pat. No. 3,564,040 describes a method to maintain the steady-state concentration of 2PN below 5 mole percent as based on the nitriles present in the reaction mixture. Because trans-2PN is difficult to separate from a mixture of 3PN and 4PN by distillation due to their close relative volatilities, the disclosed method involves the catalytic isomerization of trans-2PN to cis-2PN followed by fractional distillation of the mixture of pentenenitrile isomers to remove the more volatile cis-2PN isomer. The catalyst systems used to isomerize trans-2PN to cis-2PN are those that also serve to hydrocyanate pentenenitriles to ADN, in particular, nickel catalysts derived from monodentate phosphite ligands as described in U.S. Pat. Nos. 3,496,217 and 3,496,218.

Alternative catalyst systems for the isomerization of trans-2PN to cis-2PN are disclosed in U.S. Pat. Nos. 3,852,325 and 3,852,327. The primary advantage of the catalyst systems described therein is in avoiding appreciable carbon-carbon double bond migration in the pentenenitrile isomers, which allows for the isomerization of trans-2PN to cis-2PN without substantial further isomerization of the 3PN to 2PN. The catalysts described in U.S. Pat. No. 3,852,325 are compounds of the general formula $R_3C$—X, such as triphenylmethyl bromide, wherein R is an aryl radical having up to 18 carbon atoms and —X is of the group consisting of —H, —Cl, —Br, —I, —SH, —B(C_6H_5)_4, —PF_6, —AsF_6, —SbF_6 and —BF_4, while the catalyst systems described in U.S. Pat. No. 3,852,327 are Lewis acid/Lewis base compositions, such as combinations of zinc chloride with triphenylphosphine.

A different method of removing the 2PN from mixtures of pentenenitrile isomers containing 3PN and 4PN is disclosed in U.S. Pat. No. 3,865,865. The 2PN and/or 2-methyl-2-butenenitriles (2M2BN) can be selectively separated from a mixture of pentenenitrile isomers containing 3PN and 4PN by contacting the mixture of nitriles with an aqueous solution of a treating agent comprising sulfite and bisulfite ions and ammonium or alkali metal cations to produce an aqueous phase containing the bisulfite adduct of the 2PN and/or 2M2BN and an organic phase containing the 3PN and 4PN, substantially free of 2PN and 2M2BN. The recovered organic phase can provide a feed material of pentenenitriles for further hydrocyanation to produce ADN with greatly reduced amounts of the undesired by-product 2PN that is detrimental to catalyst efficiency.

U.S. Pat. No. 6,127,567 discloses nickel catalyst precursor compositions derived from bidentate phosphite ligands and processes for the hydrocyanation of monoethylenically unsaturated compounds which are more rapid, selective, efficient, and stable than prior processes using nickel catalysts derived from monodentate phosphites. U.S. Pat. No. 5,688, 986 discloses that at least one member of this class of catalysts is capable of hydrocyanating olefins conjugated to nitriles, for example 2PN. The present invention provides novel processes for the hydrocyanation of pentenenitriles to produce dinitriles, in particular ADN, using certain catalyst precursor compositions described in U.S. Pat. No. 6,127,567 as well as other catalyst precursor compositions. Such processes can overcome the detrimental effect of 2PN on catalyst efficiency and can greatly reduce or eliminate yield losses to 2PN in the pentenenitrile hydrocyanation reaction.

SUMMARY OF THE INVENTION

In a first aspect, the present invention provides a hydrocyanation process to produce adiponitrile and other dinitriles having six carbon atoms, the process comprising: a) forming a reaction mixture in the presence of at least one Lewis acid, said reaction mixture comprising ethylenically unsaturated nitriles having five carbon atoms, hydrogen cyanide, and a catalyst precursor composition, by continuously feeding the unsaturated nitriles, the hydrogen cyanide, and the catalyst precursor composition; b) controlling X and Z, wherein X is the overall feed molar ratio of 2-pentenenitriles to all unsaturated nitriles; and Z is the overall feed molar ratio of hydrogen cyanide to all unsaturated nitriles; by selecting a value for X in the range from about 0.001 to about 0.5; and a value for Z in the range of about 0.5 to about 0.99; such that the value of quotient Q, wherein $$Q = \frac{X}{[(\text{moles } 3PN + 4PN \text{ in the feed})/(\text{moles all unsaturated nitriles in the feed})] - Z}$$

is in the range from about 0.2 to about 10, wherein 3PN is 3-pentenenitriles and 4PN is 4-pentenenitrile; and c) withdrawing a reaction product mixture comprising adiponitrile; wherein the ratio of the concentration of 2-pentenenitriles to the concentration of 3-pentenenitriles in the reaction mixture is in the range of about 0.2/1 to about 10/1; wherein the catalyst precursor composition comprises a zero-valent nickel and at least one multidentate phosphorus-containing ligand, wherein the multidentate phosphorus-containing ligand is selected from the group consisting of a phosphite, a phosphonite, a phosphinite, a phosphine, and a mixed phosphorus-containing ligand or a combination of such members; and wherein the multidentate phosphorus-containing ligand gives acceptable results according to at least one protocol of the 2-Pentenenitrile (2PN) Hydrocyanation Test Method.

Another aspect of the present invention is the process wherein the selected value for X is in the range from about 0.01 to about 0.25, and the selected value of Z is in the range from about 0.70 to about 0.99; and wherein the value of Q is in the range from about 1 to about 5; and wherein the ratio of the concentration of 2-pentenenitriles to the concentration of 3-pentenenitriles in the reaction mixture is from about 1/1 to about 5/1.

Another aspect of the present invention is the process wherein the overall feed molar ratio of 2-pentenenitriles to all unsaturated nitriles is controlled by addition of 2-pentenenitriles produced in an independent process or by direct recycle of the 2-pentenenitriles from the reaction product mixtures within the process.

Another aspect of the present invention is the process wherein the 2-pentenenitriles originate from a pentenenitrile hydrocyanation process.

Another aspect of the present invention is the process wherein the 3-pentenenitriles originate from a 1,3-butadiene hydrocyanation process.

Another aspect of the present invention is the process wherein the multidentate phosphorus-containing ligand is a phosphite.

Another aspect of the present invention is the process wherein the multidentate phosphorus-containing ligand is a phosphonite.

Another aspect of the present invention is the process wherein the multidentate phosphorus-containing ligand is a phosphinite.

Another aspect of the present invention is the process wherein the multidentate phosphorus-containing ligand is a phosphine.

Another aspect of the present invention is the process wherein the multidentate phosphorus-containing ligand is a mixed phosphorus-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

Another aspect of the present invention is the process wherein the Lewis acid promoter comprises at least one compound selected from the group consisting of zinc chloride, iron (II) chloride, manganese (II) chloride, and mixtures thereof.

Another aspect of the present invention is the process wherein the temperature of the reaction mixture is maintained from about 20° C. to about 90° C.

Another aspect of the present invention is the process wherein the temperature of the reaction mixture is maintained from about 35° C. to about 70° C.

Another aspect of the present invention is the process wherein the catalyst precursor composition further comprises at least one monodentate phosphorus-containing ligand selected from the group consisting of a phosphite, a phosphonite, a phosphinite, and a phosphine, or a combination of such members.

Another aspect of the present invention is the process wherein the multidentate phosphorus-containing ligand is a bidentate phosphite.

Another aspect of the present invention is the process wherein the multidentate phosphorus-containing ligand is a bidentate phosphonite.

Another aspect of the present invention is the process wherein the multidentate phosphorus-containing ligand is a bidentate phosphinite.

Another aspect of the present invention is the process wherein the multidentate phosphorus-containing ligand is a bidentate phosphine.

Another aspect of the present invention is the process wherein the multidentate phosphorus-containing ligand is a bidentate mixed phosphorus-containing ligand selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

By utilizing the above catalyst precursor compositions, it has now been found that, in the hydrocyanation reaction of ethylenically unsaturated nitriles having five carbon atoms to produce ADN and other dinitriles having six carbon atoms, the yield losses due to the concurrent production of 2PN from 3PN can be greatly reduced or eliminated through the control of the ratio of the concentration of 2PN to the concentration of 3PN, in the reaction mixture, from about 0.2/1 to about 10/1.

Control of the ratio of the concentration of 2PN to the concentration of 3PN in the reaction mixture can be achieved by both controlling X, the overall feed molar ratio of 2PN to all unsaturated nitriles, and controlling Z, the overall feed molar ratio of hydrogen cyanide (HCN) to all unsaturated nitriles. X and Z can be controlled by selecting a value for X in the range from about 0.001 to about 0.5 and by selecting a value for Z in the range from about 0.5 to about 0.99, such that the value of quotient Q, wherein $$Q = \frac{X}{[(\text{moles } 3PN + 4PN \text{ in the feed})/(\text{moles all unsaturated nitriles in the feed})] - Z}$$

is in the range from about 0.2 to about 10, wherein 3PN is 3-pentenenitriles and 4PN is 4-pentenenitrile. When the ratio of the concentration of 2PN to the concentration of 3PN in the reaction mixture is controlled from about 1/1 to about 5/1, for example, X and Z can be controlled by selecting a value for X in the range from about 0.01 to about 0.25 and by selecting a value for Z in the range from about 0.70 to about 0.99, such that the value of the quotient Q is in the range from about 1 to about 5.

Such novel pentenenitrile hydrocyanation processes to produce ADN can overcome the prior art limitations of maintaining the steady-state concentrations of 2PN below 5 mole percent (based on the nitriles present in the reaction mixture) by employing the above catalyst precursor compositions, which can be expected to be more rapid, selective, efficient, and stable than prior catalyst derived from monodentate phosphite ligands used in the hydrocyanation of ethylenically unsaturated compounds. Advantageously, a single zero-valent nickel catalyst system and far less process equipment can be utilized for conversion of 2PN to the valuable products 3PN, 4PN, and ADN. The process of the present invention also allows for control of the overall feed molar ratio of 2PN to all unsaturated nitriles by direct recycle of the 2PN from the reaction product mixture within the process or by addition of 2PN produced in an independent process. Potential advantages of such a process can include the elimination of investment for a cis-2-pentenenitrile distillation column (see for example column 8 in the drawing for U.S. Pat. No. 3,564,040, wherein stream 9 from column 5 is fed directly to the pentenenitrile hydrocyanation reactor 2) and of the associated variable and fixed costs for operating said column.

DETAILED DESCRIPTION OF THE INVENTION

The present invention provides a process for the hydrocyanation of ethylenically unsaturated nitriles having five carbon atoms to produce adiponitrile and other dinitriles having six carbon atoms. ADN is of particular interest because it is a commercially versatile and important intermediate in the industrial production of nylon polyamides useful in forming films, fibers and molded articles.

As used herein, the term "ethylenically unsaturated nitriles having five carbon atoms" means pentenenitriles and methylbutenenitriles. As used herein, the term "unsaturated nitriles" also means pentenenitriles and methylbutenenitriles.

As used herein, the terms "2PN", "2-pentenenitrile", and "2-pentenenitriles" include both cis-2-pentenenitrile (cis-2PN) and trans-2-pentenenitrile (trans-2PN), unless otherwise specified. Similarly, the terms "3PN", "3-pentenenitrile," and "3-pentenenitriles" include both cis-3-pentenenitrile (cis-3PN) and trans-3-pentenenitrile (trans-3PN), unless otherwise specified. The term "4PN" refers to 4-pentenenitrile.

The ethylenically unsaturated nitriles having five carbon atoms can be prepared by the reaction of hydrogen cyanide (HCN) with 1,3-butadiene (BD). Using transition metal complexes with

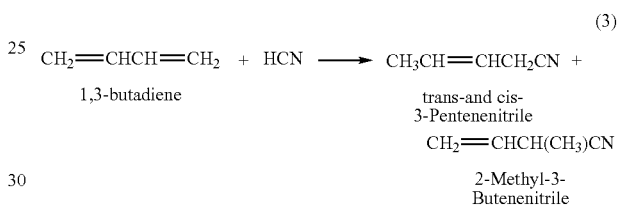

(3)

monodentate phosphites (for example, U.S. Pat. Nos. 3,496,215; 3,631,191; 3,655,723; and 3,766,237) and zero-valent nickel catalysts with multidentate phosphite ligands (for example, U.S. Pat. Nos. 5,821,378; 5,981,772; 6,020,516; and 6,284,865), the predominant linear pentenenitrile product formed by the hydrocyanation of BD is trans-3PN. As described in the prior art, the branched BD hydrocyanation product, 2-methyl-3-butenenitrile (2M3BN), can be isomerized to predominantly trans-3PN using the same catalyst compositions employed for the hydrocyanation of BD. See, for example, U.S. Pat. Nos. 3,536,748 and 3,676,481. The predominant trans-3PN product from the hydrocyanation of BD and isomerization of 2M3BN can also contain smaller quantities of 4PN, cis-3PN, 2PN, and 2M2BN isomers.

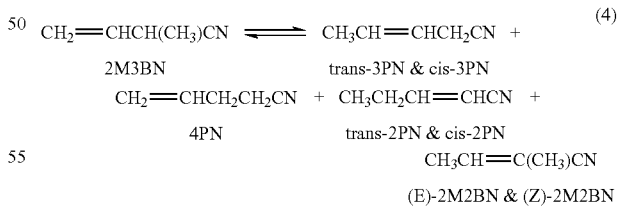

(4)

The 2PN useful in the present invention can be made in larger quantities during the hydrocyanation of 3PN and/or 4PN to form ADN, among other dinitriles, from the concurrent isomerization of 3PN to 2PN, as described in the prior art. Separation of the cis-2PN isomer by the fractional distillation of mixtures of pentenenitrile isomers, as disclosed in the art, can provide a source of isolated 2PN to be used with the present invention. See, for example, U.S. Pat. No. 3,852,327. Alternatively, the cis-2PN need not be isolated from mixtures of pentenenitrile isomers. For example, 2PN mixtures comprising 2PN, 3PN, and 4PN may be separated by vacuum distillation from the pentenenitrile hydrocyanation reaction product comprising unreacted pentenenitriles, ADN and other six carbon dinitriles, catalyst, and promoter, by methods known in the art. The 2PN mixture, as a distillation column sidestream or overhead make, may then be recycled directly to the pentenenitrile hydrocyanation process. Alternatively, the hydrocyanation reaction process of the present invention may be operated at sufficiently high conversion of pentenenitriles to enable the pentenenitrile hydrocyanation reaction product, comprising unreacted pentenenitriles, ADN and other six carbon dinitriles, catalyst, and promoter, to be fed directly to a liquid-liquid extraction process as described, for example, in U.S. Pat. No. 6,936,171, wherein the pentenenitrile to dinitrile molar ratio is from about 0.01 to about 2.5. 2PN Mixtures, comprising 2PN, 3PN, and 4PN, recovered, for example, by distillation of the extract, raffinate, or extract and raffinate phases of these liquid-liquid extraction processes may also be recycled to the pentenenitrile hydrocyanation process of the present invention.

The hydrocyanation process to produce ADN and other dinitriles having six carbon atoms is performed in the presence of at least one Lewis acid and using a catalyst precursor composition comprising a zero-valent nickel and at least one multidentate phosphorus-containing (P-containing) ligand, wherein the P-containing ligand is selected from the group consisting of a phosphite, a phosphonite, a phosphinite, a phosphine, and a mixed phosphorus-containing ligand or a combination of such members. As used herein, the term "mixed phosphorus-containing ligand" means a multidentate phosphorus-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

Each catalyst precursor composition useful in the present invention may be considered a "precursor" composition in that the zero-valent nickel at some point becomes bound to at least one multidentate P-containing ligand, and further in all likelihood, additional reactions occur during hydrocyanation, such as, for example, complexing of the initial catalyst composition to an ethylenically unsaturated compound.

As used herein, the term "catalyst precursor composition" also includes within its meaning recycled catalyst, that is, a catalyst precursor composition comprising a zero-valent nickel and at least one multidentate P-containing ligand which, having been used in the process of the invention, is returned or may be returned to the process and used again.

The catalyst precursor composition may further comprise at least one monodentate P-containing ligand selected from the group consisting of a phosphite, a phosphonite, a phosphinite, and a phosphine or a combination of such members, provided that the monodentate P- of a phosphite, a phosphonite, a phosphinite, and a phosphine or a combination of such members, provided that the monodentate P-containing ligand does not detract from the beneficial aspects of the invention. The monodentate P-containing ligand may be present as an impurity from synthesis of the multidentate P-containing ligand, or the monodentate P-containing ligand may be added as an additional component of the catalyst precursor composition.

The catalyst precursor composition may also further comprise at least one Lewis acid promoter.

The term "hydrocarbyl" is well known in the art and designates a hydrocarbon molecule from which at least one hydrogen atom has been removed. Such molecules can contain single, double, or triple bonds.

The term "aryl" is well known in the art and designates an aromatic hydrocarbon molecule from which at least one hydrogen atom has been removed.

Examples of suitable aryl groups include those containing 6 to 10 carbon atoms, which can be unsubstituted or singly or multiply substituted. Suitable substituents include, for example, $C_1$-$C_4$ hydrocarbyl, or halogen such as fluorine, chlorine or bromine, or halogenated hydrocarbyl such as trifluoromethyl, or aryl such as phenyl.

The P-containing ligand may be multidentate, for example bidentate, or tridentate. The P-containing ligand may be selected from the group consisting of a phosphite, a phosphonite, a phosphinite, a phosphine, and a mixed P-containing ligand or a combination of such members. The multidentate P-containing ligand may be represented by Formula I

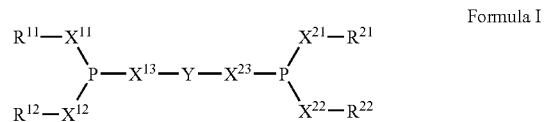

Formula I wherein
$X^{11}$, $X^{12}$, $X^{13}$, $X^{21}$, $X^{22}$, $X^{23}$ independently represent oxygen or a single bond,
$R^{11}$, $R^{12}$ independently represent identical or different, single or bridged organic radicals,
$R^{21}$, $R^{22}$ independently represent identical or different, single or bridged organic radicals, and
Y represents a bridging group.

It is to be understood that Formula I may represent a single compound or a mixture of different compounds having the indicated structure.

In one embodiment, all of the groups $X^{11}$, $X^{12}$, $X^{13}$, $X^{21}$, $X^{22}$, $X^{23}$ may represent oxygen. In such a case, the bridging group Y is joined to phosphite groups. In such a case, the multidentate P-containing ligand represented by Formula I is a phosphite.

In another embodiment, $X^{11}$ and $X^{12}$ may each represent oxygen, and $X^{13}$, a single bond; or $X^{11}$ and $X^{13}$ may each represent oxygen and $X^{12}$, a single bond, so that the phosphorus atom surrounded by $X^{11}$, $X^{12}$, and $X^{13}$ is the central atom of a phosphonite. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{21}$ and $X^{22}$ may each represent oxygen and $X^{23}$, a single bond; or $X^{21}$ and $X^{23}$ may each represent oxygen and $X^{22}$, a single bond, so that the phosphorus atom surrounded by $X^{21}$, $X^{22}$, and $X^{23}$ may be the central atom of a phosphonite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}$, $X^{22}$, and $X^{23}$ may be the central atom of a phosphinite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphite, the multidentate ligand represented by Formula I is a phosphite-phosphonite and is an example of a mixed P-containing ligand. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphonite, the multidentate P-containing ligand represented by Formula I is a phosphonite. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphinite, the multidentate P-containing ligand represented by Formula I is a phosphonite-phosphinite and is an example of a mixed P-containing ligand. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphine, the multidentate P-containing ligand represented by Formula I is a phosphonite-phosphine and is an example of a mixed P-containing ligand.

In another embodiment, $X^{13}$ may represent oxygen and $X^{11}$ and $X^{12}$, each a single bond; or $X^{11}$ may represent oxygen and $X^{12}$ and $X^{13}$, each a single bond, so that the phosphorus atom surrounded by $X^{11}$, $X^{12}$, and $X^{13}$ is the central atom of a phosphinite. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}$, $X^{22}$, and $X^{23}$ may be the central atom of a phosphinite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphite, the multidentate P-containing ligand represented by Formula I is a phosphite-phosphinite and is an example of a mixed P-containing ligand. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphinite, the multidentate P-containing ligand represented by Formula I is a phosphinite. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphine, the multidentate P-containing ligand represented by Formula I is a phosphinite-phosphine and is an example of a mixed P-containing ligand.

In another embodiment, $X^{11}$, $X^{12}$, and $X^{13}$ may each represent a single bond, so that the phosphorus atom surrounded by $X^{11}$, $X^{12}$, and $X^{13}$ is the central atom of a phosphine. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphine and the phosphorus atom surrounded by $X^{21}$, $X^{22}$, and $X^{23}$ is the central atom of a phosphite, the multidentate P-containing ligand represented by Formula I is a phosphite-phosphine and is an example of a mixed P-containing ligand. When the phosphorus atom surrounded by $X^{11}$, $X^{12}$, and $X^{13}$ is the central atom of a phosphine and the phosphorus atom surrounded by $X^{21}$, $X^{22}$, and $X^{23}$ is the central atom of a phosphine, the multidentate P-containing ligand represented by Formula I is a phosphine.

Bridging group Y may be aryl groups substituted, for example, with $C_1$-$C_4$ hydrocarbyl, or halogen such as fluorine, chlorine, or bromine, or halogenated hydrocarbyl such as trifluoromethyl, or aryl such as phenyl, or unsubstituted aryl groups, for example those with 6 to 20 carbon atoms in the aromatic system, for example 2,2'-biphenyl and 1,1'-bi-2-naphthyl.

Radicals $R^{11}$ and $R^{12}$ may independently represent identical or different organic radicals. $R^{11}$ and $R^{12}$ may be aryl radicals, for example those containing 6 to 10 carbon atoms, which can be unsubstituted or singly or multiply substituted, for example by $C_1$-$C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{21}$ and $R^{22}$ may independently represent identical or different organic radicals. $R^{21}$ and $R^{22}$ may be aryl radicals, for example those containing 6 to 10 carbon atoms, which can be unsubstituted or singly or multiply substituted, for example by $C_1$-$C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{11}$ and $R^{12}$ may be single or bridged. Radicals $R^{21}$ and $R^{22}$ may also be single or bridged. Radicals $R^{11}$, $R^{12}$, $R^{21}$, and $R^{22}$ may all be single, or two may be bridged and two single, or all four may be bridged in the manner described.

Examples of multidentate P-containing ligands may include the following:

1) the compounds of Formula I, II, III, IV, and V disclosed in U.S. Pat. No. 5,723,641;
2) the compounds of Formula I, II, III, IV, V, VI, and VII disclosed in U.S. Pat. No. 5,512,696, for example the compounds used in Examples 1 through 31 therein;
3) the compounds of Formula I, II, III, IV, V, VI, VII, VIII, IX, X, XI, XII, XIII, XIV, and XV disclosed in U.S. Pat. No. 5,821,378, for example the compounds used in Examples 1 through 73 therein;
4) the compounds of Formula I, II, III, IV, V, and VI disclosed in U.S. Pat. No. 5,512,695, for example the compounds used in Examples 1 through 6 therein;
5) the compounds of Formula I, II, III, IV, V, VI, VII, VIII, IX, X, XI, XII, XIII, and XIV disclosed in U.S. Pat. No. 5,981,772, for example the compounds used in Examples 1 through 66 therein;
6) the compounds disclosed in U.S. Pat. No. 6,127,567, for example the compounds used in Examples 1 through 29 therein;
7) the compounds of Formula I, II, III, IV, V, VI, VII, VIII, IX, and X disclosed in U.S. Pat. No. 6,020,516, for example the compounds used in Examples 1 through 33 therein;
8) the compounds disclosed in U.S. Pat. No. 5,959,135, for example the compounds used in Examples 1 through 13 therein;
9) the compounds of Formula I, II, and III disclosed in U.S. Pat. No. 5,847,191;
10) the compounds disclosed in U.S. Pat. No. 5,523,453, for example the compounds of Formula 1, 2, 3, 4, 5, 6, 7, 8, 9, 10, 11, 12, 13, 14, 15, 16, 17, 18, 19, 20, and 21 therein;
11) the compounds disclosed in U.S. Pat. No. 5,693,843, for example the compounds of Formula I, II, III, IV, V, VI, VII, VIII, IX, X, XI, XII, and XIII, for example the compounds used in Examples 1 through 20 therein;
12) the compounds of Formula V, VI, VII, VIII, IX, X, XI, XII, XIII, XIV, XV, XVI, XVII, XVIII, XIX, XX, XXI, XXII, XXIII, XXIV, XXV, and XXVI disclosed in U.S. Pat. No. 6,893,996;
13) the compounds disclosed in published patent application WO 01/14392, for example the compounds illustrated in Formula V, VI, VII, VII, IX, X, XI, XII, XIII, XIV, XV, XVI, XVII, XXI, XXII, and XXIII therein;

14) the chelating compounds disclosed in U.S. Pat. No. 6,242,633, for example the compounds of Formula If, Ig, and Ih;
15) the compounds disclosed in U.S. Pat. No. 6,521,778, for example the compounds of Formula I, Ia, Ib, and Ic, for example the compounds referred to as Ligand I and II;
16) the compounds disclosed in published patent application WO 02/13964, for example the compounds of Formula Ia, Ib, Ic, Id, Ie, If, Ig, Ih, Ii, Ij, and Ik, for example the compounds referred to as Ligand 1, 2, 3, 4, 5, and 6;
17) the compounds disclosed in German Patent Application DE 100 460 25;
18) the chelating compounds disclosed in U.S. Pat. No. 7,022,866, for example the compounds of Formula 1 and 2, for example the compounds referred to as Ligand 1 and 2;
19) the compounds disclosed in United States Published Patent Application No. 2005/0090677, for example the compounds of Formula 1, 1a, 1b, 1c, 1d, 1e, 1f, 1g, 1h, 1i, 1j, 1k, 1l, 1m, 1n, 1o, 2, and 3;
20) the compounds disclosed in United States Published Patent Application No. 2005/0090678, for example the compounds of Formula 1 and 2, for example the compounds referred to as Ligand 1, 2, 3, 4, 5, and 6;
21) the compounds disclosed in published patent application WO 2005/042547, for example the compounds of Formula 1, 1a, 1b, 1c, 1d, 1e, 1f, 1g, 1h, 1i, 1j, 1k, 1l, 1m, 1n, 1o, 2, 3, 4, 5, and 6, for example the compounds referred to as Ligand 1, 2, 3, and 4;
22) the chelating compounds disclosed in U.S. Pat. No. 6,169,198, for example the compounds of Formula I; and
23) the compounds disclosed in U.S. Pat. No. 6,660,877, for example the compounds of Formula I, II, and III, for example the compounds used in Examples 1 through 25 therein.

These references also disclose methods for preparing multidentate ligands of Formula I.

Further examples of multidentate P-containing ligands may include a bidentate phosphite ligand selected from a member of the group represented by Formulas II and III, in which all like reference characters have the same meaning, except as further explicitly limited:

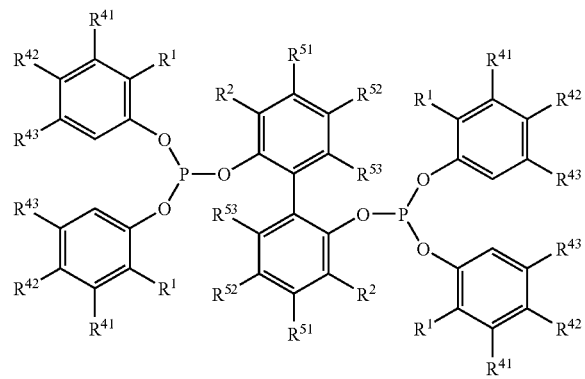

Formula II

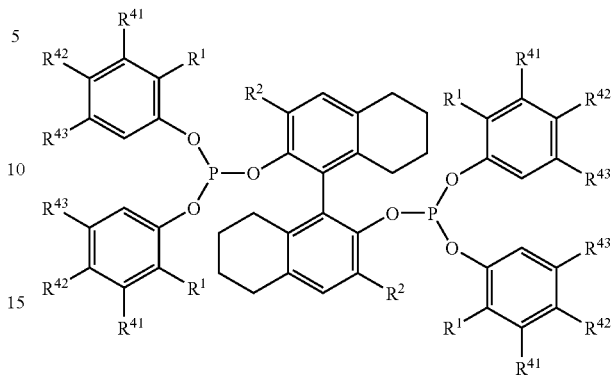

Formula III wherein
each $R^1$ is independently selected from the group consisting of methyl, ethyl, and primary hydrocarbyl of 3 to 6 carbon atoms;
each $R^2$ is independently selected from the group consisting of primary and secondary hydrocarbyl of 1 to 6 carbon atoms; and
each $R^{41}$, $R^{42}$, $R^{43}$, $R^{51}$, $R^{52}$, and $R^{53}$ is independently selected from the group consisting of H, aryl, and a primary, secondary, or tertiary hydrocarbyl of 1 to 6 carbon atoms.

It will be recognized that Formula II and Formula III are two dimensional representations of three-dimensional molecules and that rotation about chemical bonds can occur in the molecules to give configurations differing from those shown. For example, rotation about the carbon-carbon bond between the 2- and 2'-positions of the biphenyl and octahydrobinaphthyl bridging groups of Formula II and Formula III, respectively, can bring the two phosphorus atoms of each Formula in closer proximity to one another and can allow the phosphite ligand to bind to a single nickel atom in a bidentate fashion. The term "bidentate" is well known in the art and means both phosphorus atoms of the ligand are bonded to a single nickel atom.

Some examples of ligands useful in the catalyst precursor compositions of the present invention are generally described in U.S. Pat. Nos. 6,171,996 and 5,512,696 and are illustrated above by Formula II and Formula III, as defined above. In one Formula II ligand (Ligand "A" in the Examples), each $R^1$ is methyl, each $R^2$ is isopropyl, each $R^{41}$, $R^{42}$, $R^{43}$ and $R^{51}$ is hydrogen, and each $R^{52}$ and $R^{53}$ is methyl. In another Formula II ligand (Ligand "B" in the Examples), each $R^1$ is methyl, each $R^2$ is isopropyl, each $R^{41}$, $R^{43}$ and $R^{51}$ is hydrogen, and each $R^{42}$, $R^{52}$ and $R^{53}$ is methyl. In one Formula III ligand (Ligand "C" in the Examples), each $R^1$ is methyl, each $R^2$ is isopropyl, and each $R^{41}$, $R^{42}$ and $R^{43}$ is hydrogen.

The multidentate P-containing ligand may also be a polymeric ligand composition, as disclosed, for example, in U.S. Pat. No. 6,284,865; U.S. Pat. No. 6,924,345, or United States Published Patent Application No. 2003/135014. Methods for preparing such polymeric ligand compositions are well known in the art and are disclosed, for example, in the above cited references.

The catalyst precursor composition may further comprise at least one monodentate P-containing ligand selected from the group consisting of a phosphite, a phosphonite, a phosphinite, and a phosphine or a combination of such members. The monodentate P-containing ligand may be added as an additional component of the catalyst precursor composition, or it may be present, for example, as an impurity from the synthesis of the multidentate P-containing ligand. The monodentate P-containing ligand may be represented by Formula IV $$P(X^1R^{31})(X^2R^{32})(X^3R^{33}) \qquad \text{Formula IV}$$

wherein $X^1$, $X^2$, $X^3$ independently represent oxygen or a single bond, and $R^{31}$, $R^{32}$, $R^{33}$ independently represent identical or different, single or bridged organic radicals.

is to be understood that Formula IV may be a single compound or a mixture of different compounds having the indicated structure.

In one embodiment, all of the groups $X^1$, $X^2$, and $X^3$ may represent oxygen, so that Formula IV represents a phosphite of formula $P(OR^{31})(OR^{32})(OR^{33})$, wherein $R^{31}$, $R^{32}$, and $R^{33}$ have the meanings defined herein.

If one of the groups $X^1$, $X^2$, and $X^3$ represents a single bond and two groups represent oxygen, Formula IV represents a phosphonite of formula $P(OR^{31})(OR^{32})(R^{33})$, $P(R^{31})(OR^{32})(OR^{33})$, or $P(OR^{31})(R^{32})(OR^{33})$, wherein $R^{31}$, $R^{32}$, and $R^{33}$ have the meanings defined herein.

If two of the groups $X^1$, $X^2$, and $X^3$ represent single bonds and one group represents oxygen, Formula IV represents a phosphinite of formula $P(OR^{31})(R^{32})(R^{33})$ or $P(R^{31})(OR^{32})(R^{33})$ or $P(R^{31})(R^{32})(OR^{33})$, wherein $R^{31}$, $R^{32}$, and $R^{33}$ have the meanings defined herein.

The groups $X^1$, $X^2$, $X^3$ may independently represent oxygen or a single bond. If all the groups $X^1$, $X^2$, and $X^3$ represent single bonds, Formula IV represents a phosphine of formula $P(R^{31}R^{32}R^{33})$, wherein $R^{31}$, $R^{32}$, and $R^{33}$ have the meanings defined herein.

The groups $R^{31}$, $R^{32}$, and $R^{33}$ may independently represent identical or different organic radicals, for example hydrocarbyl radicals comprising 1 to 10 carbon atoms, such as methyl, ethyl, n-propyl, isopropyl, n-butyl, isobutyl, s-butyl, and t-butyl, aryl groups such as phenyl, o-tolyl, m-tolyl, p-tolyl, 1-naphthyl, or 2-naphthyl, or hydrocarbyl radicals comprising 1 to 20 carbon atoms, such as 1,1'-biphenol or 1,1'-binaphthol. The $R^{31}$, $R^{32}$, and $R^{33}$ radicals may be connected to one another directly, meaning not solely via the central phosphorus atom. Alternatively, the $R^{31}$, $R^{32}$, and $R^{33}$ radicals may be not directly connected to one another.

For example, $R^{31}$, $R^{32}$, and $R^{33}$ may be selected from the group composed of phenyl, o-tolyl, m-tolyl, and p-tolyl. As another example, a maximum of two of the $R^{31}$, $R^{32}$, and $R^{33}$ groups may be phenyl. Alternatively, a maximum of two of the $R^{31}$, $R^{32}$, and $R^{33}$ groups may be o-tolyl.

Compounds of Formula IVa, $$(\text{o-tolyl-O-})_w(\text{m-tolyl-O-})_x(\text{p-tolyl-O-})_y(\text{phenyl-O-})_zP \qquad \text{Formula IVa}$$

may be used as the monodentate P-containing ligand, wherein w, x, y, and z are integers, and the following conditions apply: w+x+y+z=3 and w, z≦2.

Examples of compounds of Formula IVa include (p-tolyl-O-)(phenyl-O—)$_2$P, (m-tolyl-O-)(phenyl-O—)$_2$P, (o-tolyl-O-)(phenyl-O—)$_2$P, (p-tolyl-O-)2(phenyl-O—)P, (m-tolyl-O-)$_2$(phenyl-O—)P, (o-tolyl-O-)$_2$(phenyl-O—)P, (m-tolyl-O-)(p-tolyl-O-)(phenyl-O—)P, (o-tolyl-O-)(p-tolyl-O-)(phenyl-O—)P, (o-tolyl-O-)(m-tolyl-O-)(phenyl-O—)P, (p-tolyl-O—)$_3$P, (m-tolyl-O-)(p-tolyl-O-)$_2$P, (o-tolyl-O-)(p-tolyl-O—)$_2$P, (m-tolyl-O-)$_2$(p-tolyl-O—)P, (o-tolyl-O-)$_2$(p-tolyl-O—)P, (o-tolyl-O-)(m-tolyl-O-)(p-tolyl-O—)P, (m-tolyl-O—)$_3$P, (o-tolyl-O-)(m-tolyl-O—)$_2$P, (o-tolyl-O-)$_2$(m-tolyl-O—)P, or mixtures of such compounds.

Mixtures containing (m-tolyl-O—)$_3$P, (m-tolyl-O-)$_2$(p-tolyl-O—)P, (m-tolyl-O-)(p-tolyl-O—)$_2$P, and (p-tolyl-O—)$_3$P may be obtained, for example, by reacting a mixture containing m-cresol and p-cresol, in particular in a molar ratio of 2:1 as occurs in the distillative processing of crude oil, with a phosphorus trihalide such as phosphorus trichloride.

Additional examples of monodentate P-containing ligands are the phosphites disclosed in U.S. Pat. No. 6,770,770 and referred to herein as phosphites of Formula IVb, $$P(OR^{31})_x(OR^{32})_y(OR^{33})_z(OR^{34})_p \qquad \text{Formula IVb}$$

wherein $R^{31}$ is an aromatic radical having a $C_1$-$C_{18}$ alkyl substituent in the o-position relative to the oxygen atom which connects the phosphorus atom to the aromatic system, or having an aromatic substituent in the o-position relative to the oxygen atom which connects the phosphorus atom to the aromatic system, or having an aromatic system fused on in the o-position relative to the oxygen atom which connects the phosphorus atom to the aromatic system;

$R^{32}$ is an aromatic radical having a $C_1$-$C_{18}$ alkyl substituent in the m-position relative to the oxygen atom which connects the phosphorus atom to the aromatic system, or having an aromatic substituent in the m-position relative to the oxygen atom which connects the phosphorus atom to the aromatic system, or having an aromatic system fused on in the m-position relative to the oxygen atom which connects the phosphorus atom to the aromatic system, where the aromatic radical bears a hydrogen atom in the o-position relative to the oxygen atom which connects the phosphorus atom to the aromatic system;

$R^{33}$ is an aromatic radical having a $C_1$-$C_{18}$ alkyl substituent in the p-position relative to the oxygen atom which connects the phosphorus atom to the aromatic system, or having an aromatic substituent in the p-position relative to the oxygen atom which connects the phosphorus atom to the aromatic system, where the aromatic radical bears a hydrogen atom in the o-position relative to the oxygen atom which connects the phosphorus atom to the aromatic system;

$R^{34}$ is an aromatic radical which bears substituents other than those defined for $R^{31}$, $R^{32}$, and $R^{33}$ in the o-, m-, and p-position relative to the oxygen atom which connects the phosphorus atom to the aromatic system, where the aromatic radical bears a hydrogen atom in the o-position relative to the oxygen atom which connects the phosphorus atom to the aromatic system;

x is 1 or 2; and y, z, and p independently of one another is 0, 1, or 2, provided that x+y+z+p=3.

Examples of radical $R^{31}$ include o-tolyl, o-ethylphenyl, o-n-propylphenyl, o-isopropylphenyl, o-n-butylphenyl, o-sec-butylphenyl, o-tert-butylphenyl, (o-phenyl)-phenyl, or 1-naphthyl groups.

Examples of radical $R^{32}$ include m-tolyl, m-ethylphenyl, m-propylphenyl, m-isopropylphenyl, m-n-butylphenyl, m-sec-butylphenyl, m-tert-butylphenyl, (m-phenyl)-phenyl, or 2-naphthyl groups.

Examples of radical $R^{33}$ include p-tolyl, p-ethylphenyl, p-n-propylphenyl, p-isopropylphenyl, p-n-butylphenyl, p-sec-butylphenyl, p-tert-butylphenyl, or (p-phenyl)-phenyl groups.

Radical $R^{34}$ may be, for example, phenyl, and p may be zero. The indices x, y, z, and p in compounds of Formula IVb may have the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of Formula IVb are those in which p is zero, and $R^{31}$, $R^{32}$, and $R^{33}$ are independently selected from o-isopropylphenyl, m-tolyl, and p-tolyl, and $R^{34}$ is phenyl.

Additional examples of phosphites of Formula IVb are those in which $R^{31}$ is the o-isopropylphenyl radical, $R^{32}$ is the m-tolyl radical, and $R^{33}$ is the p-tolyl radical, with the indices listed in the above table; also those in which $R^{31}$ is the o-tolyl radical, $R^{32}$ is the m-tolyl radical, and $R^{33}$ is the p-tolyl radical, with the indices listed in the table; also those in which $R^{31}$ is the 1-naphthyl radical, $R^{32}$ is the m-tolyl radical, and $R^{33}$ is the p-tolyl radical, with the indices listed in the table; also those in which $R^{31}$ is the o-tolyl radical, $R^{32}$ is the 2-naphthyl radical, and $R^{33}$ is the p-tolyl radical, with the indices listed in the table; and lastly, those in which $R^{31}$ is the o-isopropylphenyl radical, $R^{32}$ is the 2-naphthyl radical, and $R^{33}$ is the p-tolyl radical, with the indices listed in the table; and mixtures of these phosphites.

In one embodiment, the catalyst precursor composition may comprise a zero-valent nickel, at least one multidentate P-containing ligand selected from the group consisting of a phosphite, a phosphonite, a phosphinite, a phosphine, and a mixed P-containing ligand or a combination of such members, and at least one monodentate P-containing ligand selected from tritolyl phosphite and phosphites of Formula IVb

                                              Formula IVb wherein $R^{31}$, $R^{32}$, and $R^{33}$ are independently selected from o-isopropylphenyl, m-tolyl, and p-tolyl, $R^{34}$ is phenyl, x is 1 or 2, and y, z, p are independently 0, 1, or 2, provided that x+y+z+p=3; and mixtures thereof.

A multidentate P-containing ligand is suitable for use in the process of the invention if it gives acceptable results according to at least one protocol of the 2PN Hydrocyanation Test Method specified herein. The 2PN Hydrocyanation Test Method utilizes three protocols which differ in the method of HCN delivery to the reaction mixture. A catalyst precursor composition comprising a zero-valent nickel and the multidentate P-containing ligand is first prepared by combining the zero-valent nickel compound $Ni(COD)_2$, wherein COD is 1,5-cyclooctadiene, with the multidentate P-containing ligand in toluene solvent. The resulting catalyst precursor composition is then contacted with a solution comprising cis-2PN and a Lewis acid promoter. The next step is to contact this reaction solution with anhydrous, uninhibited HCN at about 50° C. for about 16 hours according to one of three protocols. The mole ratio of promoter to nickel present in the reaction mixture is about 0.96/1; the mole ratio of multidentate P-containing ligand to zero-valent nickel in the reaction mixture is in the range of about 1/1 to about 1.2/1; and the initial mole ratio of 2PN to nickel is about 110/1 to about 130/1.

Acceptable results according to the 2PN Hydrocyanation Test Method are those wherein the 2PN (that is, cis-2PN and trans-2PN) conversion to dinitriles is at least 0.1% according to at least one protocol of the 2PN Hydrocyanation Test Method. Also included in the 2PN conversion is the conversion to dinitriles of any 3PN and/or 4PN derived from isomerization of the 2PN. As used herein, the term dinitriles includes ADN, MGN, and 2-ethylsuccinonitrile. An analytical method such as gas chromatography can be used to determine the amounts of dinitriles produced. Acceptable results according to the 2PN Hydrocyanation Test Method are indicative of a ligand or a ligand mixture's ability to form an active catalyst, within a catalyst precursor composition, to convert cis-2PN to useful products, such as dinitriles, 3PN, and 4PN, under the conditions of the 2PN Hydrocyanation Test Method.

The multidentate P-containing ligands useful in the catalyst precursor compositions employed in the present invention may be prepared by any suitable synthetic means known in the art, for example as disclosed in at least some of the references disclosing examples of multidentate P-containing ligands. For example, the multidentate P-containing ligands of Formula II may be synthesized as described in U.S. Pat. No. 6,171,996, which is incorporated herein by reference. For Ligand "A," for example, the reaction of two equivalents of o-cresol with phosphorus trichloride gives the corresponding phosphorochloridite. The reaction of the phosphorochloridite with 3,3'-di-iso-propyl-5,5',6,6'-tetra-methyl-2,2'-biphenol in the presence of triethylamine gives Ligand "A." The crude bidentate phosphite ligand can be worked up by the process described in U.S. Pat. No. 6,069,267, which is incorporated herein by reference. As disclosed therein, the bidentate phosphite ligand product mixture can typically contain the desired product in about 70% to about 90% selectivity, with other phosphite by-products such as monodentate phosphites making up the balance of the product mixture. The bidentate phosphite ligand itself or these bidentate/monodentate phosphite ligand mixtures are suitable for use with the present invention.

The multidentate P-containing ligand itself or mixtures of the multidentate P-containing ligand and at least one monodentate P-containing ligand are suitable for use with the present invention.

The catalyst precursor compositions employed for this process should ideally be substantially free of carbon monoxide, oxygen, and water and may be preformed or prepared in situ according to techniques well known in the art, as also described in U.S. Pat. No. 6,171,996. The catalyst precursor composition may be formed by contacting the multidentate P-containing ligand with a zero-valent nickel compound having ligands easily displaced by multidentate P-containing ligands, such as $Ni(COD)_2$, $Ni[P(O\text{-}o\text{-}C_6H_4CH_3)_3]_3$, and $Ni[P(O\text{-}o\text{-}C_6H_4CH_3)_3]_2(C_2H_4)$, all of which are well known in the art, wherein 1,5-cyclooctadiene (COD), tris(ortho-tolyl)phosphite [$P(O\text{-}o\text{-}C_6H_4CH_3)_3$], and ethylene ($C_2H_4$) are the easily displaced ligands. Elemental nickel, preferably nickel powder, when combined with a halogenated catalyst, as described in U.S. Pat. No. 3,903,120, is also a suitable source of zero-valent nickel. Alternatively, divalent nickel compounds may be combined with a reducing agent, to serve as a source of zero-valent nickel in the reaction, in the presence of the multidentate P-containing ligands. Suitable divalent nickel compounds include compounds of the formula $NiY_2$ where Y is halide, carboxylate or acetylacetonate. Suitable reducing agents include metal borohydrides, metal aluminum hydrides, metal alkyls, Zn, Fe, Al, Na, or $H_2$. See, for example, U.S. Pat. No. 6,893,996.

In the catalyst precursor composition, the multidentate P-containing ligand may be present in excess of what can theoretically be coordinated to the nickel at a given time, unless it detracts from the beneficial aspects of the invention. For example, the nature of the catalyst precursor compositions of ligands of Formula II and III is such that effective catalysts may be formed at any molar ratio of ligand to nickel, but the preferred range of the molar ratio of ligand to nickel is from about 1/1 to about 4/1.

The pentenenitrile hydrocyanation process performed in the present invention can be carried out in the presence of at least one Lewis acid promoter which affects both the activity and selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin, as described in the prior art. Examples include, but are not limited to, $BPh_3$, $ZnCl_2$, $CoI_2$, $SnCl_2$, $PhAlCl_2$, $Ph_3Sn(O_3SC_6H_5CH_3)$ and $Cu(O_3SCF_3)_2$. Preferred promoters include zinc chloride $ZnCl_2$, iron(II) chloride $FeCl_2$, and manganese(II) chloride $MnCl_2$, and mixtures thereof. U.S. Pat. No. 4,874,884 describes how synergistic combinations of promoters can be chosen to increase the catalytic activity of the catalyst system. The mole ratio of promoter to nickel present in the reaction can, for example, be in the range of about 0.1/1 to about 10/1, for example in the range of about 0.5/1 to about 1.2/1.

The catalyst precursor composition may be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, may be used to dissolve the catalyst precursor composition.

To maximize pentenenitrile hydrocyanation rates while minimizing catalyst consumption through active nickel oxidation by HCN, the hydrocyanation reaction of the present invention should be performed in reactor systems providing efficient mass transfer of pentenenitriles, HCN, and catalyst and efficient removal of the heat of reaction. Such reactor systems are known in the art. The hydrocyanation reaction of the present invention can, in at least one embodiment, be effectively practiced in a continuous stirred tank reactor in which the reactor product is back-mixed well with the reaction mixture. In such a reactor system, the kinetics of the hydrocyanation reaction may be expected to be primarily governed by the reactor product composition. In another suitable embodiment, the hydrocyanation reaction of the present invention can be practiced in the reactor system disclosed in U.S. Pat. No. 4,382,038. In this reactor system, the primary reaction zone comprises a plurality of stages in series with the product from one stage continuously directed to a subsequent stage and the HCN added to each stage. The effluent from the primary reaction zone, comprising zero-valent nickel catalyst, unreacted pentenenitriles, unreacted HCN, and the dinitrile products is then sent to a secondary reaction zone where its temperature can be controlled and where no HCN is added to the effluent.

The continuous hydrocyanation reaction can, for example, be conducted between about 20° C. to about 90° C., for example in the range of about 35° C. to about 70° C.

While atmospheric pressure is satisfactory for carrying out the present invention, higher and lower pressures can be used. In this regard, pressures of from about 0.5 to about 10 atmospheres (about 50.7 to about 1013 kPa), for example, may be used. Higher pressures, up to 20,000 kPa or more, may be used, if desired, but any benefit that may be obtained thereby may not be justified in view of the increased cost of such operations.

HCN, substantially free of carbon monoxide, oxygen, ammonia, and water can be introduced to the reaction as a vapor, liquid, or mixtures thereof. As an alternative, a cyanohydrin can be used as the source of HCN. See, for example, U.S. Pat. No. 3,655,723.

The overall feed molar ratio of HCN to zero-valent nickel may, for example, be in the range of about 100/1 to about 3000/1, for example in the range of about 300/1 to about 2000/1. At reactor startup, the reaction vessel may be partially charged, for example, with either a solution of a catalyst precursor composition in substrate pentenenitriles or the reactor product from a previous reaction campaign, followed by the initiation of all reactor feeds. Continuous reactor product removal may begin upon establishing the desired fluid levels within the reaction vessel. The unreacted pentenenitriles, ADN and other six carbon dinitrile reaction products and components of the catalyst precursor composition can be recovered by conventional techniques known in the art, such as, for example, by liquid-liquid extraction as disclosed in U.S. Pat. No. 6,936,171, and by distillation.

At least one potential advantage of using the catalyst precursor compositions described above for the hydrocyanation of ethylenically unsaturated nitrites with reduced yield losses from the concurrent isomerization of 3PN to 2PN may be realized when the ratio of the concentration of 2PN to the concentration of 3PN in the reaction mixture is maintained from about 0.2/1 to about 10/1. Control of the ratio of the concentration of 2PN to the concentration of 3PN in the reaction mixture in this range can be established by controlling X, the overall feed molar ratio of 2PN to all unsaturated nitrites, by selecting a value for X in the range from about 0.001 to about 0.5, and controlling Z, the overall feed molar ratio of HCN to all unsaturated nitrites, by selecting a value for Z in the range from about 0.5 to about 0.99, such that the value of quotient Q, wherein $$Q = \frac{X}{[(\text{moles } 3PN + 4PN \text{ in the feed})/(\text{moles all unsaturated nitriles in the feed})] - Z}$$

is in the range from about 0.2 to about 10, wherein 3PN is 3-pentenenitriles and 4PN is 4-pentenenitrile. Similarly, reduced yield losses from the concurrent isomerization of 3PN to 2PN may be realized when the ratio of the concentration of 2PN to the concentration of 3PN in the reaction mixture is maintained from about 1/1 to about 5/1. Control of this ratio in this range can be established by controlling X and Z by selecting a value for X in the range from about 0.01 to about 0.25, and by selecting a value for Z in the range from about 0.70 to about 0.99, such that Q is in the range from about 1 to about 5.

While not limited to any particular method, establishing the overall feed molar ratio of 2PN to all unsaturated nitrites may be accomplished by at least two different methods and/or combinations thereof. For example, the overall feed molar ratio of 2PN to all unsaturated nitrites can be controlled by addition of 2PN produced in an independent process or by direct recycle of the 2PN from the reaction product mixture within the process. The first method involves obtaining 2PN produced by a different process or prepared in a separate manufacturing facility. The desired feed molar ratio may then be achieved by blending the 2PN thus obtained with the other substrate pentenenitrile isomers in the appropriate proportions. Alternatively, the 2PN can originate from a pentenenitrile hydrocyanation process. For example, the 2PN in the reactor product of the present invention may be physically separated, along with the other unreacted unsaturated nitriles, from the dinitrile product and catalyst, for example, by vacuum distillation. The recovered 2PN may be recycled and blended with the other substrate pentenenitrile isomers in the appropriate proportions to constitute a feed to the reaction of the present invention with the desired molar ratios. The 2PN can be substantially free of other nitriles, or the 2PN can be present in a process stream which comprises additional nitriles.

Embodiments falling within the scope of the present invention may be further understood in view of the following non-limiting examples

EXAMPLES

The following procedures can be used to treat cis-2PN before its use in hydrocyanation reactions. Cis-2-pentenenitrile (98%) produced from a BD and 3PN hydrocyanation process may be obtained commercially from the Sigma-Aldrich Chemical Company. Hydroperoxide impurities can be common in such a reagent and are typically detrimental to hydrocyanation catalyst performance. Hydroperoxide impurities can be measured and reduced in cis-2PN, if necessary, by titration, for example with triphenylphosphine, prior to purification by distillation. Distillation under a nitrogen atmosphere can be utilized to remove the majority of oxygen, water, and peroxides and heavy boilers by taking, for example, a forecut and a heartcut during the distillation. The purified cis-2PN of the heartcut can be transferred into a drybox filled with an inert gas such as nitrogen and can be dried further over 3A molecular sieves (which have been previously dried and degassed under nitrogen).

Bis(1,5-cyclooctadiene)nickel(0), $Ni(COD)_2$, and anhydrous $ZnCl_2$ were purchased from a commercial supplier and also stored under a nitrogen atmosphere in a drybox.

The three protocols of the 2PN Hydrocyanation Test Method are as follows. All three protocols have about 19 wt % initial c2PN.

Protocol #1, Exposure to HCN Vapor:

Under an inert atmosphere such as dry nitrogen or argon, a $Ni(COD)_2$ solution is prepared by dissolving $Ni(COD)_2$ (0.039 g) in toluene (2.79 g). A toluene solution, or other appropriate solvent solution, of the multidentate P-containing ligand or a ligand mixture comprising a multidentate P-containing ligand to be tested (0.230 mL of 0.062 mol total multidentate P-containing ligand/L of toluene) is treated with the $Ni(COD)_2$ solution (0.320 mL) and thoroughly mixed to provide a catalyst precursor solution with a zero-valent nickel/multidentate P-containing ligand molar ratio of about 1/1. A cis-2-pentenenitrile (cis-2PN)/$ZnCl_2$ solution is prepared by dissolving $ZnCl_2$ (0.017 g in 1.02 g cis-2PN). A sample of catalyst precursor solution (0.100 mL) is treated with cis-2PN/$ZnCl_2$ solution (0.025 mL); the resulting mixture has cis-2PN/nickel molar ratio of about 123 and a $ZnCl_2$/nickel molar ratio of about 0.96/1. Over a period of 16 hours, the mixture is heated to about 50 °C and exposed to HCN vapor supplied from a reservoir of uninhibited, liquid HCN at ambient temperature (619 mm Hg or 82.5 kPa vapor pressure at 20 °C). The reaction mixture is then cooled to ambient temperature, treated with acetonitrile (0.125 mL), and analyzed by gas chromatography for the amount of ADN, MGN, and 2-ethylsuccinonitrile produced, in order to calculate the percent conversion of 2PN to dinitriles.

Protocol #2, Continuous Flow of HCN Vapor Diluted with Nitrogen Over the Reaction Solution:

Under an inert atmosphere such as dry nitrogen ($N_2$) or argon, $Ni(COD)_2$ solution is prepared by dissolving $Ni(COD)_2$ (0.039 g) in toluene (2.79 g). A toluene solution, or other appropriate solvent solution, of the multidentate P-containing ligand or a ligand mixture comprising a multidentate P-containing ligand to be tested (0.230 mL of 0.062 mol total multidentate P-containing ligand/L of toluene) is treated with the $Ni(COD)_2$ solution (0.320 mL) and thoroughly mixed to provide a catalyst precursor solution with a zero-valent nickel/multidentate P-containing ligand molar ratio of about 1/1. A cis-2-pentenenitrile (cis-2PN)/$ZnCl_2$ solution is prepared by dissolving anhydrous $ZnCl_2$ (0.017 g in 1.02 g cis-2PN). A sample of catalyst precursor solution (0.100 mL) is treated with cis-2PN/$ZnCl_2$ solution (0.025 mL); the resulting mixture has cis-2PN/nickel molar ratio of about 123 and a $ZnCl_2$/nickel molar ratio of about 0.96/1. A $HCN/N_2$ gas mixture (about 35% HCN vol/vol) is produced by bubbling dry nitrogen gas through anhydrous, uninhibited, liquid HCN at 0 °C and swept (about 1 to about 5 mL min) over the catalyst precursor/c2PN mixture heated to about 50° C. After 16 hours, the reaction mixture is then cooled to ambient temperature, treated with acetonitrile (0.125 mL), and analyzed by gas chromatography for the amount of ADN, MGN, and 2-ethylsuccinonitrile produced, in order to calculate the percent conversion of 2PN to dinitriles.

Protocol #3, Sealed Vial:

Under an inert atmosphere such as dry nitrogen or argon, a $Ni(COD)_2$ solution is prepared by dissolving $Ni(COD)_2$ (0.065 g) in toluene (2.79 g). A toluene solution, or other appropriate solvent solution, of the multidentate P-containing ligand or a ligand mixture comprising a multidentate P-containing ligand to be tested (0.230 mL of 0.062 mol total multidentate P-containing ligand/L of toluene) is treated with the $Ni(COD)_2$ solution (0.320 mL) and thoroughly mixed to provide a catalyst precursor solution with a zero-valent nickel/multidentate P-containing ligand molar ratio of about 1/1. A cis-2-pentenenitrile (cis-2PN)/HCN/$ZnCl_2$ solution is prepared by combining anhydrous $ZnCl_2$ (0.0406 g), freshly distilled, uninhibited, liquid HCN (0.556 g), and cis-2PN (1.661 g). Into a 2 mL GC vial, a sample of catalyst precursor solution (0.092 mL) is treated with cis-2PN/HCN/$ZnCl_2$ solution (0.034 mL) then the vial is sealed with an aluminum septum cap; the resulting mixture has cis-2PN/nickel molar ratio of about 123, HCN/nickel molar ratio of about 123, and a $ZnCl_2$/nickel molar ratio of about 0.96/1. Over a period of 16 hours, the mixture is heated to about 50° C. The reaction mixture is then cooled to ambient temperature, treated with acetonitrile (0.125 mL), and analyzed by gas chromatography for the amount of ADN, MGN, and 2-ethylsuccinonitrile produced, in order to calculate the percent conversion of 2PN to dinitriles.

In the following Examples, unless stated otherwise, all operations were carried Out under a nitrogen atmosphere using a drybox or standard Schlenk techniques. Examples of the inventive continuous hydrocyanation process have been performed in a single-stage 18-mL glass continuous stirred-tank reactor (CSTR), the general design of which has been described in U.S. Pat. Nos. 4,371,474, 4,705,881, and 4,874,884, the entire disclosures of which are incorporated herein by reference. The reactor consisted of a crimp-baffled round bottomed glass vessel, jacketed to allow controlling the temperature of the reaction mixture with fluid flow from an external, controlled, fluid-heating temperature bath. All reagents were introduced into the reaction vessel via syringe pumps, through sidearms fitted with rubber septa. The reactor was fitted with an overflow arm through which the reaction product flowed by gravity into a product receiver. Agitation and mixing of the reaction mixture was provided by magnetic stirring. A small nitrogen purge was constantly applied to the vapor space of the reactor to maintain an inert atmosphere.

The trans-3PN (95 wt %) and cis-2PN (98 wt %) utilized in the hydrocyanation experiments described below originated from a commercial ADN plant that hydrocyanates BD and pentenenitriles. Trans-3PN and cis-2PN produced from a BD and pentenenitrile hydrocyanation process may be obtained commercially from the Sigma-Aldrich Chemical Company. Each pentenenitrile was distilled under a nitrogen atmosphere then stored in a nitrogen-filled drybox.

The Examples were performed using a catalyst precursor composition wherein the multidentate P-containing ligand was a bidentate phosphite ligand selected from a member of the group represented by Formula II or Formula III, in which all like reference characters have the same meaning, except as further explicitly limited:

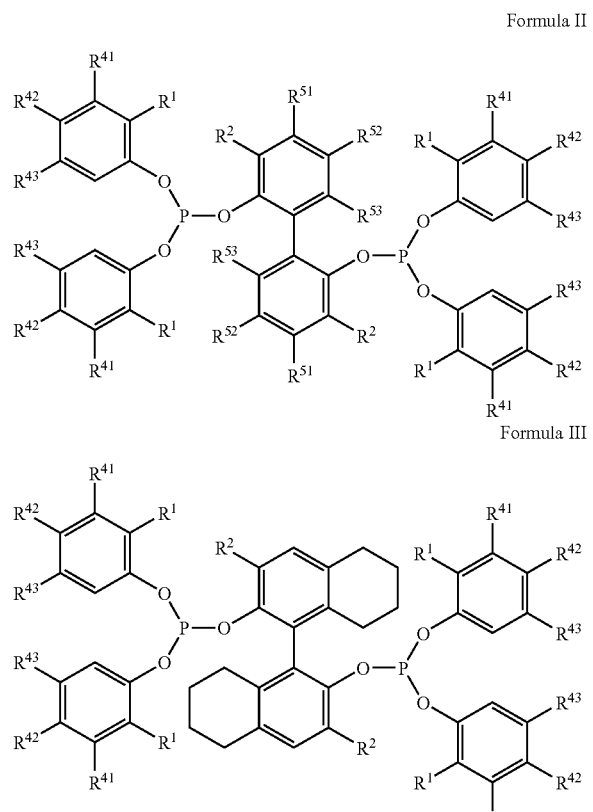

Formula II

Formula III wherein
each $R^1$ is independently selected from the group consisting of methyl, ethyl, and primary hydrocarbyl of 3 to 6 carbon atoms;
each $R^2$ is independently selected from the group consisting of primary and secondary hydrocarbyl of 1 to 6 carbon atoms; and each $R^{41}$, $R^{42}$, $R^{43}$, $R^{51}$, $R^{52}$, and $R^{53}$ is independently selected from the group consisting of H, aryl, and a primary, secondary, or tertiary hydrocarbyl of 1 to 6 carbon atoms.

Ligand "A" of the Example 1 may be prepared by any suitable synthetic means known in the art. For example, 3,3'-diisopropyl-5,5',6,6'-tetramethyl-2,2'-biphenol can be prepared by the procedure disclosed in United States Published Patent Application No. 2003/0100802, which is incorporated herein by reference, in which 4-methylthymol can undergo oxidative coupling to the substituted biphenol in the presence of a copper chlorohydroxide-TMEDA complex (TMEDA is N,N,N',N'-tetramethylethylenediamine) and air.

The phosphorochloridite of o-cresol, $(C_7H_7O)_2PCl$, can be prepared, for example, by the procedure disclosed in United States Published Patent Application No. 2004/0106815, which is incorporated herein by reference. To selectively form this phosphorochloridite, anhydrous triethylamine and o-cresol can be added separately and concurrently in a controlled manner to $PCl_3$ dissolved in an appropriate solvent under temperature-controlled conditions.

The reaction of this phosphorochloridite with the 3,3'-diisopropyl-5,5',6,6'-tetramethyl-2,2'-biphenol to form the desired Ligand "A" can be performed, for example, according to the method disclosed in U.S. Pat. No. 6,069,267, which is hereby incorporated by reference. The phosphorochloridite can be reacted with 3,3'-diisopropyl-5,5',6,6'-tetramethyl-2,2'-biphenol in the presence of an organic base to form Ligand "A", which can be isolated according to techniques well known in the art, as also described in U.S. Pat. No. 6,069,267. The monodentate phosphite impurities in Ligand "A" prepared by this method would have the following structures.

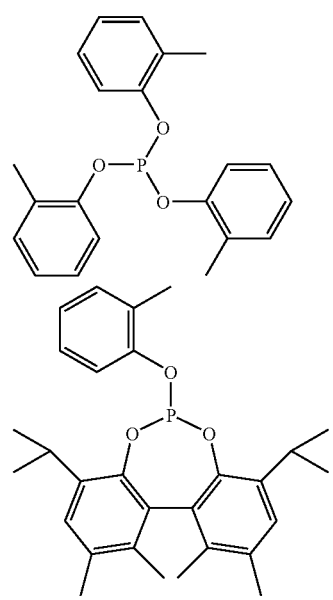

Likewise, Ligand "B" can be prepared from 3,3'-diisopropyl-5,5',6,6'-tetramethyl-2,2'-biphenol and the phosphorochloridite of 2,4-xylenol, $((C_8H_9O)_2PCl$. The monodentate phosphite impurities in Ligand "B" prepared by this method would have the following structures.

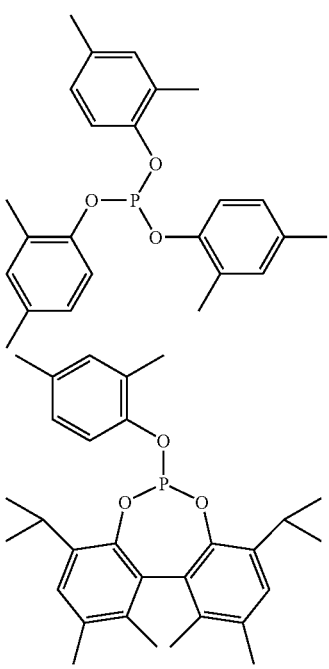

Likewise, Ligand "C" can be prepared from 3,3'-diisopropyl-5,5',6,6',7,7',8,8'-octahydro-2,2'-binaphthol, prepared by the method described in United States Patent Application No. 2003/0100803, and the phosphorochloridite of o-cresol, $(C_7H_7O)_2PCl$. The monodentate phosphite impurities in Ligand "C" prepared by this method would have the following structures.

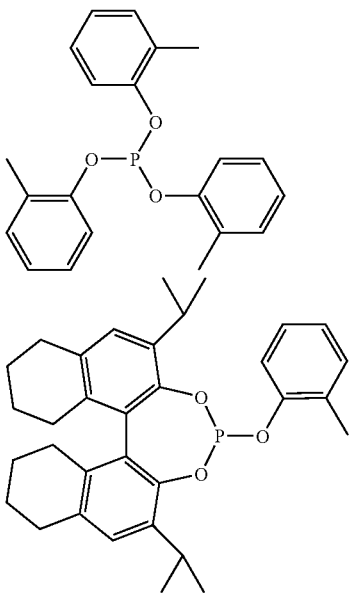

The anhydrous, uninhibited HCN feed to the reactor was delivered as a pentenenitrile (PN) solution (40% HCN by weight). The composition of the pentenenitriles used to make the feed solutions was determined by the desired pentenenitrile feed composition to the reactor. The amount of methylbutenenitriles in the pentenenitrile feed solutions was negligible. The ligand-Ni catalyst precursor composition was synthesized by the reaction of $Ni(COD)_2$ with a slight excess of the corresponding bidentate phosphite ligand (approximately 1.2 to 1.4 molar equivalents/Ni) in toluene solvent at ambient temperatures, as generally described in U.S. Pat. No. 6,120,700. After removal of the toluene solvent and volatile materials under vacuum, a corresponding quantity of anhydrous Lewis acid promoter was added to the solid residue of the catalyst precursor composition, and the entire mixture was dissolved in a corresponding mixture of pentenenitriles. The resulting pentenenitrile solution comprising catalyst precursor composition and promoter was thus fed to the reactor as described below.

At startup, the reaction vessel was charged with about 9 mL of the pentenenitrile solution comprising catalyst precursor composition and promoter. The continuous hydrocyanation reaction was then initiated by turning on the feed of both the pentenenitrile solution comprising precursor composition and promoter and the HCN solution. Periodic samples of the reactor product flowing to the receiver were analyzed by gas chromatographic (GC) analysis to determine nitrile product compositions used in calculating reactor conversions and yields.

Definitions:
PN's=all pentenenitrile isomers of empirical formula $C_5H_7N$, including all methylbutenenitrile isomers of empirical formula $C_5H_7N$
2PN=cis- and trans-2-pentenenitriles
3PN=cis- and trans-3-pentenenitriles
4PN=4-pentenenitrile
DN's=all dinitrile isomers of empirical formula $C_6H_8N_2$ (includes ADN, MGN and ESN)
ADN=adiponitrile
MGN=2-methylglutaronitrile
ESN=ethylsuccinonitrile
g/hr=gram/hour
conversion=moles reacted/moles fed
yield=moles produced/moles (3PN+4PN) reacted
mol % DN's=molar fraction DN's/(PN's+DN's) in reactor product
mol % 2PN feed=molar fraction 2PN/(PN's+DN's) in reactor feed
mol % 2PN product=molar fraction 2PN/(PN's+DN's) in reactor product
mol % 3PN product=molar fraction 3PN/(PN's+DN's) in reactor product
linearity=moles ADN/moles (ADN+MGN+ESN) produced

Example 1

The inventive continuous hydrocyanation process was demonstrated using Ligand "A," shown below, and $FeCl_2$ as the Lewis acid promoter.

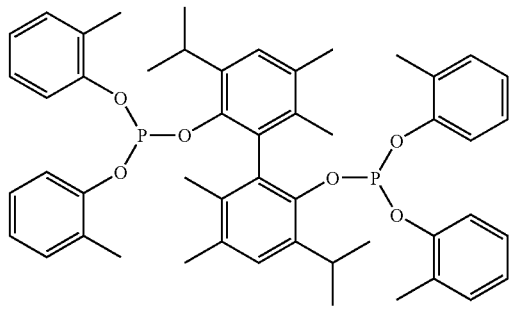

Ligand "A"

Target reaction rate=$1.6 \times 10^{-4}$ moles HCN/liter—second
Temperature=50° C.
mol % 2PN feed=12.8%

The target feed rates of the reaction components were as follows.

| Reagent | Feed Rate, g/hr |
|---|---|
| HCN[a] | 0.29 |
| 3,4PN (3PN + 4PN) | 1.01 |
| 2PN | 0.15 |
| Ni catalyst, calculated as Ni metal | 0.0010 |
| Total Ligand[b] | 0.029 |
| FeCl$_2$ promoter | 0.0015 |

Notes:
[a]HCN excluding PN solvent.
[b]Mixture of Ligand "A" and corresponding monodentate phosphites as described above.

The overall feed molar ratio of 2PN to all unsaturated nitriles was about 0.13 and the overall feed molar ratio of HCN to all unsaturated nitriles was about 0.75.

The averaged GC analyses of reactor product samples taken from 92 to 100 hours from the inception of continuous flow indicated the following steady-state results.

| 3,4PN Conversion | 86% |
|---|---|
| mol % DN's | 73.6% |
| mol % 2PN product | 14.0% |
| mol % 3PN product | 11.8% |
| 2PN Yield | 1.5% |
| Linearity | 94.2% |
| ADN Yield | 92.8% |

The ratio of the concentration of 2PN to the concentration of 3PN in the reaction mixture was about 1.2.

Example 2

The inventive continuous hydrocyanation process was demonstrated using Ligand "A" and ZnCl$_2$ as the Lewis acid promoter.
Target reaction rate=$1.6 \times 10^{-4}$ moles HCN/liter—second
Temperature=50° C.
mol % 2PN feed=20.6%

The target feed rates of the reaction components were as follows.

| Reagent | Feed Rate, g/hr |
|---|---|
| HCN[a] | 0.29 |
| 3,4PN (3PN + 4PN) | 0.94 |
| 2PN | 0.25 |
| Ni catalyst, calculated as Ni metal | 0.0013 |
| Total Ligand[b] | 0.027 |
| ZnCl$_2$ promoter | 0.0020 |

Notes:
[a]HCN excluding PN solvent.
[b]Mixture of Ligand "A" and corresponding monodentate phosphites as described above.

The overall feed molar ratio of 2PN to all unsaturated nitrites was about 0.21 and the overall feed molar ratio of HCN to all unsaturated nitrites was about 0.70.

The averaged GC analyses of reactor product samples taken from 49 to 53 hours from the inception of continuous flow indicated the following steady-state results.

| 3,4PN Conversion | 90.7% |
|---|---|
| mol % DN's | 71.9% |
| mol % 2PN product | 20.3% |
| mol % 3PN product | 7.2% |
| 2PN Yield | 0.0% |
| Linearity | 95.0% |
| ADN Yield | 95.0% |

The ratio of the concentration of 2PN to the concentration of 3PN in the reaction mixture was about 2.8.

Comparative Example A

The following is a comparative example of a continuous hydrocyanation reaction using Ligand "A" and ZnCl$_2$ as promoter without the addition of 2PN to the reactor feed.
Target reaction rate=$2.3 \times 10^{-4}$ moles HCN/liter—second
Temperature=50° C.
mol % 2PN feed=0.1% [c]

The target feed rates of the reaction components were as follows.

| Reagent | Feed Rate, g/hr |
|---|---|
| HCN[a] | 0.38 |
| 3,4PN (3PN + 4PN) | 1.63 |
| 2PN | 0.0016 |
| Ni catalyst, calculated as Ni metal | 0.0018 |
| Total Ligand[b] | 0.045 |
| ZnCl$_2$ promoter | 0.0048 |

Notes:
[a]HCN excluding PN solvent.
[b]Mixture of Ligand "A" and corresponding monodentate phosphites as described above.
[c]2PN impurity in the 3PN feed material.

The overall feed molar ratio of 2PN to all unsaturated nitrites was about 0.001 and the overall feed molar ratio of HCN to all unsaturated nitrites was about 0.70.

The averaged GC analyses of reactor product samples taken from 46 to 54 hours from the inception of continuous flow indicated the following steady-state results.

| 3,4PN Conversion | 71.1% |
|---|---|
| mol % DN's | 68.7% |
| mol % 2PN product | 2.1% |
| mol % 3PN product | 28.0% |
| 2PN Yield | 2.5% |
| Linearity | 94.9% |
| ADN Yield | 92.5% |

The ratio of the concentration of 2PN to the concentration of 3PN in the reaction mixture was about 0.08.

Example 3

The inventive continuous hydrocyanation process was demonstrated using Ligand "B," shown below, and FeCl$_2$ as the Lewis acid promoter.

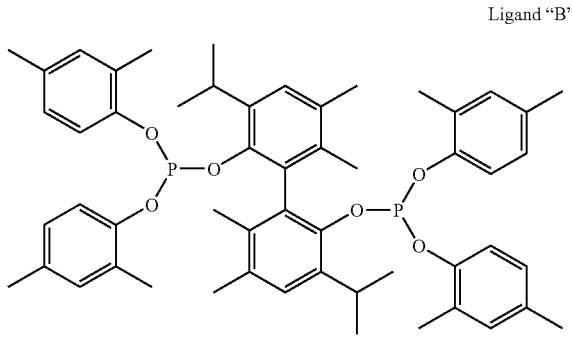

Ligand "B"

Target reaction rate=$1.6 \times 10^{-4}$ moles HCN/liter—second
Temperature=50° C.
mol % 2PN feed=15.4%

The target feed rates of the reaction components were as follows.

| Reagent | Feed Rate, g/hr |
|---|---|
| HCN[a] | 0.29 |
| 3,4PN (3PN + 4PN) | 0.95 |
| 2PN | 0.175 |
| Ni catalyst, calculated as Ni metal | 0.0013 |
| Total Ligand[b] | 0.029 |
| FeCl$_2$ promoter | 0.0019 |

Notes:
[a] HCN excluding PN solvent.
[b] Mixture of Ligand "B" and corresponding monodentate phosphites as described above.

The overall feed molar ratio of 2PN to all unsaturated nitrites was about 0.15 and the overall feed molar ratio of HCN to all unsaturated nitriles was about 0.80.

The averaged GC analyses of reactor product samples taken from 69 to 78 hours from the inception of continuous flow indicated the following steady-state results.

| | |
|---|---|
| 3,4PN Conversion | 92.3% |
| mol % DN's | 77.4% |
| mol % 2PN product | 15.6% |
| mol % 3PN product | 6.4% |
| 2PN Yield | 0.3% |
| Linearity | 94.7% |
| ADN Yield | 94.4% |

The ratio of the concentration of 2PN to the concentration of 3PN in the reaction mixture was about 2.4.

Example 4

The inventive continuous hydrocyanation process was demonstrated using Ligand "B" and ZnCl$_2$ as the Lewis acid promoter.
Target reaction rate=$1.6 \times 10^{-4}$ moles HCN/liter—second
Temperature=50° C.
mol % 2PN feed=14.9%

The target feed rates of the reaction components were as follows.

| Reagent | Feed Rate, g/hr |
|---|---|
| HCN[a] | 0.29 |
| 3,4PN (3PN + 4PN) | 0.96 |
| 2PN | 0.17 |
| Ni catalyst, calculated as Ni metal | 0.0013 |
| Total Ligand[b] | 0.029 |
| ZnCl$_2$ promoter | 0.0020 |

Notes:
[a] HCN excluding PN solvent.
[b] Mixture of Ligand "B" and corresponding monodentate phosphites as described above.

The overall feed molar ratio of 2PN to all unsaturated nitrites was about 0.15 and the overall feed molar ratio of HCN to all unsaturated nitriles was about 0.77.

The averaged GC analyses of reactor product samples taken from 66 to 73 hours from the inception of continuous flow indicated the following steady-state results.

| | |
|---|---|
| 3,4PN Conversion | 90.7% |
| mol % DN's | 76.2% |
| mol % 2PN product | 15.5% |
| mol % 3PN product | 7.7% |
| 2PN Yield | 0.7% |
| Linearity | 95.4% |
| ADN Yield | 94.7% |

The ratio of the concentration of 2PN to the concentration of 3PN in the reaction mixture was about 2.0.

Comparative Example B

The following is a comparative example of a continuous hydrocyanation reaction using Ligand "B" and ZnCl$_2$ as promoter without the addition of 2PN to the reactor feed.
Target reaction rate=$2.3 \times 10^{-4}$ moles HCN/liter—second
Temperature=50° C.
mol % 2PN feed=0.3% [c]

The target feed rates of the reaction components were as follows.

| Reagent | Feed Rate, g/hr |
|---|---|
| HCN[a] | 0.38 |
| 3,4PN (3PN + 4PN) | 1.63 |
| 2PN | 0.0049 |
| Ni catalyst, calculated as Ni metal | 0.0018 |
| Total Ligand[b] | 0.049 |
| ZnCl$_2$ promoter | 0.0048 |

Notes:
[a] HCN excluding PN solvent.
[b] Mixture of Ligand "B" and corresponding monodentate phosphites as described above.
[c] 2PN impurity in the 3PN feed material.

The overall feed molar ratio of 2PN to all unsaturated nitrites was about 0.003 and the overall feed molar ratio of HCN to all unsaturated nitriles was about 0.70.

The averaged GC analyses of reactor product samples taken from 45 to 48 hours from the inception of continuous flow indicated the following steady-state results.

| | |
|---|---|
| 3,4PN Conversion | 73.9% |
| mol % DN's | 71.5% |
| mol % 2PN product | 2.1% |
| mol % 3PN product | 25.2% |
| 2PN Yield | 2.5% |
| Linearity | 95.4% |
| ADN Yield | 93.0% |

The ratio of the concentration of 2PN to the concentration of 3PN in the reaction mixture was about 0.08.

Example 5

The inventive continuous hydrocyanation process was demonstrated using Ligand "C," shown below, and $ZnCl_2$ as the Lewis acid promoter.

Ligand "C"

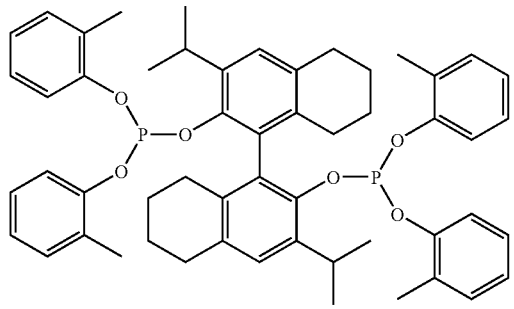

Target reaction rate=$1.6 \times 10^{-4}$ moles HCN/liter—second
Temperature=50° C.
mol % 2PN feed=20.4%

The target feed rates of the reaction components were as follows.

| Reagent | Feed Rate, g/hr |
|---|---|
| HCN[a] | 0.29 |
| 3,4PN (3PN + 4PN) | 0.94 |
| 2PN | 0.24 |
| Ni catalyst, calculated as Ni metal | 0.0013 |
| Total Ligand[b] | 0.029 |
| $ZnCl_2$ promoter | 0.0020 |

Notes:
[a]HCN excluding PN solvent.
[b]Mixture of Ligand "C" and corresponding monodentate phosphites as described above.

The overall feed molar ratio of 2PN to all unsaturated nitriles was about 0.20 and the overall feed molar ratio of HCN to all unsaturated nitriles was about 0.73.

The averaged GC analyses of reactor product samples taken from 71 to 79 hours from the inception of continuous flow indicated the following steady-state results.

| | |
|---|---|
| 3,4PN Conversion | 90.0% |
| mol % DN's | 70.4% |
| mol % 2PN product | 21.1% |
| mol % 3PN product | 7.9% |
| 2PN Yield | 1.0% |
| Linearity | 95.0% |
| ADN Yield | 94.1% |

The ratio of the concentration of 2PN to the concentration of 3PN in the reaction mixture was about 2.7.

Comparative Example C

The following is a comparative example of a continuous hydrocyanation reaction using Ligand "C" and $ZnCl_2$ as promoter without the addition of 2PN to the reactor feed.
Target reaction rate=$2.3 \times 10^{-4}$ moles HCN/liter—second
Temperature=50° C.
mol % 2PN feed=0.4% [c]

The target feed rates of the reaction components were as follows.

| Reagent | Feed Rate, g/hr |
|---|---|
| HCN[a] | 0.40 |
| 3,4PN (3PN + 4PN) | 1.70 |
| 2PN | 0.0068 |
| Ni catalyst, calculated as Ni metal | 0.0019 |
| Total Ligand[b] | 0.051 |
| $ZnCl_2$ promoter | 0.0050 |

Notes:
[a]HCN excluding PN solvent.
[b]Mixture of Ligand "C" and corresponding monodentate phosphites as described above.
[c]2PN impurity in the 3PN feed material.

The overall feed molar ratio of 2PN to all unsaturated nitrites was about 0.004 and the overall feed molar ratio of HCN to all unsaturated nitrites was about 0.70.

The averaged GC analyses of reactor product samples taken from 48 to 53 hours from the inception of continuous flow indicated the following steady-state results.

| | |
|---|---|
| 3,4PN Conversion | 72.6% |
| mol % DNs | 70.3% |
| mol % 2PN product | 2.1% |
| mol % 3PN product | 26.6% |
| 2PN Yield | 2.4% |
| Linearity | 94.9% |
| ADN Yield | 92.6% |

The ratio of the concentration of 2PN to the concentration of 3PN in the reaction mixture was about 0.08.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:
1. A hydrocyanation process to produce adiponitrile and other dinitriles having six carbon atoms, the process comprising:
a) forming a reaction mixture in the presence of at least one Lewis acid, said reaction mixture comprising ethyleni- cally unsaturated nitriles having five carbon atoms, hydrogen cyanide, and a catalyst precursor composition, by continuously feeding the ethylenically unsaturated nitriles, the hydrogen cyanide, and the catalyst precursor composition;

b) controlling X and Z,
  wherein X is the overall feed molar ratio of 2-pentenenitriles to all unsaturated nitriles; and
  Z is the overall feed molar ratio of hydrogen cyanide to all unsaturated nitriles;
  by selecting
    a value for X in the range of 0.001 to 0.5; and
    a value for Z in the range of 0.5 to 0.99;
  such that the value of quotient Q, wherein $$Q = \frac{X}{[(\text{moles } 3PN + 4PN \text{ in the feed})/(\text{moles all unsaturated nitriles in the feed})] - Z}$$

is in the range from 0.2 to 10, wherein 3PN is 3-pentenenitriles and 4PN is 4-pentenenitrile; and
c) withdrawing a reaction product mixture comprising adiponitrile;

wherein the ratio of the concentration of 2-pentenenitriles to the concentration of 3-pentenenitriles in the reaction mixture is in the range from 0.2/1 to 10/1;
wherein the catalyst precursor composition comprises a zerovalent nickel and at least one multidentate phosphorus-containing ligand;
wherein the multidentate phosphorus-containing ligand is selected from the group consisting of a phosphite, a phosphonite, a phosphinite, a phosphine, and a mixed phosphorus-containing ligand or a combination of such members; and
wherein the multidentate phosphorus-containing ligand gives acceptable results according to at least one protocol of the 2-Pentenenitrile Hydrocyanation Test Method.

2. The process of claim 1,
  wherein the selected value for X is in the range from 0.01 to 0.25 and the selected value for Z is in the range from 0.70 to 0.99; and wherein the value of 0 is in the range from 1 to 5; and
  wherein the ratio of the concentration of 2-pentenenitriles to the concentration of 3-pentenenitriles in the reaction mixture is in the range from 1/1 to 5/1.

3. The process of claim 2, wherein the multidentate phosphorus-containing ligand is a phosphite.

4. The process of claim 2, wherein the multidentate phosphorus-containing ligand is a phosphonite.

5. The process of claim 2, wherein the multidentate phosphorus-containing ligand is a phosphinite.

6. The process of claim 2, wherein the multidentate phosphorus-containing ligand is a phosphine.

7. The process of claim 2, wherein the multidentate phosphorus-containing ligand is a mixed phosphorus-containing ligand comprising at least one combination selected from the group consisting of a phosphite-phosphonite, a phosphite phosphinite, a phosphite-phosphine, a phosphonite-phosphinite, a phosphonite-phosphine, and a phosphinite-phosphine or a combination of such members.

8. The process of claim 1 wherein the overall feed molar ratio of 2-pentenenitriles to all unsaturated nitriles is controlled by addition of 2-pentenenitriles produced in an independent process or by direct recycle of the 2-pentenenitriles from the reaction product mixture within the process.

9. The process of claim 1 wherein the Lewis acid promoter comprises at least one compound selected from the group consisting of zinc chloride, iron (II) chloride, manganese (II) chloride, and mixtures thereof.

10. The process of claim 1 wherein the temperature of the reaction mixture is maintained from 20° C. to 90° C.

11. The process of claim 1 wherein the temperature of the reaction mixture is maintained from 35° C. to 70° C.

12. The process of claim 1 wherein the 2-pentenenitriles originate from a pentenenitrile hydrocyanation process.

13. The process of claim 1 wherein the 3-pentenenitriles originate from a 1,3-butadiene hydrocyanation process.

14. The process of claim 1 wherein the catalyst precursor composition further comprises at least one monodentate phosphorus-containing ligand selected from the group consisting of a phosphite, a phosphonite, a phosphinite, and a phosphine or a combination of such members.

15. The process according to claim 1, wherein the multidentate phosphorus-containing ligand is a bidentate phosphite.

16. The process according to claim 1, wherein the multidentate phosphorus-containing ligand is a bidentate phosphonite.

17. The process according to claim 1, wherein the multidentate phosphorus-containing ligand is a bidentate phosphinite.

18. The process according to claim 1, wherein the multidentate phosphorus-containing ligand is a bidentate phosphine.

19. The process according to claim 1, wherein the multidentate phosphorus-containing ligand is a bidentate mixed phosphorus-containing ligand selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

* * * * *